US008565861B2

(12) United States Patent
Taira et al.

(10) Patent No.: US 8,565,861 B2
(45) Date of Patent: Oct. 22, 2013

(54) OPTICAL INSPECTION DEVICE, ELECTROMAGNETIC WAVE DETECTION METHOD, ELECTROMAGNETIC WAVE DETECTION DEVICE, ORGANISM OBSERVATION METHOD, MICROSCOPE, ENDOSCOPE, AND OPTICAL TOMOGRAPHIC IMAGE GENERATION DEVICE

(75) Inventors: Kenji Taira, Tokyo (JP); Hiroyoshi Yajima, Kanagawa (JP); Shinichi Takimoto, Tokyo (JP)

(73) Assignee: Olympus Corporation, Tokyo (JP)

(*) Notice: Subject to any disclaimer, the term of this patent is extended or adjusted under 35 U.S.C. 154(b) by 514 days.

(21) Appl. No.: 12/678,390

(22) PCT Filed: Mar. 23, 2009

(86) PCT No.: PCT/JP2009/055654
§ 371 (c)(1),
(2), (4) Date: Mar. 16, 2010

(87) PCT Pub. No.: WO2009/133734
PCT Pub. Date: Nov. 5, 2009

(65) Prior Publication Data
US 2010/0210952 A1    Aug. 19, 2010

(30) Foreign Application Priority Data

May 2, 2008  (JP) ................................. 2008-120293
May 2, 2008  (JP) ................................. 2008-120331
Mar. 4, 2009  (JP) ................................. 2009-051172

(51) Int. Cl.
*A61B 6/00*    (2006.01)
(52) U.S. Cl.
USPC .......................................... 600/476; 600/478

(58) Field of Classification Search
USPC ........................... 600/476, 478; 356/450, 401
See application file for complete search history.

(56) References Cited

U.S. PATENT DOCUMENTS 4,945,531 A * 7/1990 Suzuki ............................. 398/91
4,967,144 A * 10/1990 Aoshima et al. ................ 324/96

(Continued)

FOREIGN PATENT DOCUMENTS

JP    2002-95663    4/2002
JP    2003-90792    3/2003

OTHER PUBLICATIONS

International Search Report dated Jun. 9, 2009.

(Continued)

*Primary Examiner* — Tse Chen
*Assistant Examiner* — Joel F Brutus
(74) *Attorney, Agent, or Firm* — Scully, Scott, Murphy & Presser, P.C.

(57) ABSTRACT

An optical inspection device 1, comprising a light generation means 2, a light irradiation means 3 irradiating an object to be inspected 4 with light generated from the light generation means 2 and a photodetection means 6 photoelectrically converting signal light obtained from the object to be inspected 4 through irradiation of light by the light irradiation means 3, and inspecting the object to be inspected 4 based on output from the photodetection means 6, wherein a light amplification means 5 amplifying signal light obtained from the object to be inspected 4 is provided. There is thus provided an optical inspection device capable of photoelectrically converting signal light from the object to be inspected with high sensitivity and promptly with its inexpensive configuration without increasing the intensity of light with which the object to be inspected is irradiated and without using an expensive low-noise and high-sensitivity photodetector.

18 Claims, 26 Drawing Sheets

(56) References Cited

U.S. PATENT DOCUMENTS

| | | | |
|---|---|---|---|
| 5,004,341 A * | 4/1991 | Grynberg et al. | 356/459 |
| 5,579,154 A * | 11/1996 | Mueller-Fiedler et al. | 359/341.1 |
| 5,589,936 A * | 12/1996 | Uchikawa et al. | 356/450 |
| 6,043,922 A * | 3/2000 | Koga et al. | 398/213 |
| 6,423,956 B1 | 7/2002 | Mandella et al. | |
| 6,493,492 B1 | 12/2002 | Fischer | |
| 6,592,822 B1 | 7/2003 | Chandler | |
| 2001/0043332 A1 * | 11/2001 | Toida | 356/479 |
| 2002/0191911 A1 | 12/2002 | Ukraincyk et al. | |
| 2003/0197920 A1 * | 10/2003 | Nakano | 359/341.3 |
| 2004/0181148 A1 * | 9/2004 | Uchiyama et al. | 600/425 |

OTHER PUBLICATIONS

Extended Supplementary European Search Report dated Mar. 30, 2011.

EPC Communication dated Nov. 14, 2012 in the corresponding European Patent Application No. EP 09 738 671.8.

* cited by examiner

OPTICAL INSPECTION DEVICE, ELECTROMAGNETIC WAVE DETECTION METHOD, ELECTROMAGNETIC WAVE DETECTION DEVICE, ORGANISM OBSERVATION METHOD, MICROSCOPE, ENDOSCOPE, AND OPTICAL TOMOGRAPHIC IMAGE GENERATION DEVICE

CROSS REFERENCE TO RELATED APPLICATION

This application claims priority to and the benefit of Japan Patent Application No. 2008-120331 filed on May 2, 2008, Japan Patent Application No. 2008-120293 filed on May 2, 2008 and Japan Patent Application No. 2009-051172 filed on Mar. 4, 2009, the entire content of which is incorporated herein by reference.

TECHNICAL FIELD

This invention relates to an optical inspection device, an electromagnetic wave detection method, an organism observation method, a microscope, an endoscope and the like. Furthermore, this invention relates to an optical tomographic image generation device irradiating an object to be inspected with light whose wavelength varies with time to generate a tomographic image of the object to be inspected.

BACKGROUND ART

Generally, in various systems using light such as image observation, a sensor, security, laser radar and the like, the technique of detecting desired light is a fundamental and important element significantly influencing their performance. In particular, the needs for the detection technique with high speed and high sensitivity are high.

For example, there has been traditionally and widely used an optical inspection method in which an organism is irradiated with light and then the transmitted light, reflected light or scattered light is detected to extract in vivo information from such detected signal light. In particular, the optical imaging technique, two-dimensionally scanning a region to be inspected with light and displaying information of obtained signal light as an image, contributes greatly to the field of medicine.

Moreover, in accordance with the development of laser technique, there are recently being active the biological or medical studies using laser scanning-type imaging such as a laser scanning-type microscope, a laser scanning-type microscopic endoscope or the like. In particular, the laser scanning-type fluorescent imaging method enables serial observation of living cells at a high signal-to-noise ratio, thus being an essential tool for biological or medical studies. Among such methods, the multiphoton fluorescent imaging method using multiphoton excitation when obtaining fluorescence enables observation of deep portion of an organism, thus drawing attention as a new fluorescent imaging method (see Non-Patent Documents 1, 2, for example).

Moreover, there is getting active the research development of a laser scanning-type imaging method using nonlinear optical effects in organisms such as Coherent anti-Stokes Raman Scattering (CARS) imaging (see Non-Patent Document 3, for example), high-frequency generating imaging (see Non-Patent Document 4) or the like. Since the laser scanning imaging method using the nonlinear optical effects does not require dyeing of a sample to be observed with fluorescent substances such as fluorescent protein, fluorescent dye or the like, the method has an advantage, as compared with the fluorescent imaging method, that the true state of organisms can be observed.

In this connection, in the optical imaging for organisms including the laser scanning-type imaging, optical signals obtained from an organism sample are usually weak due to influences by light scattering effects and light absorbing effects in the organism sample, or the like. Particularly in the imaging method using nonlinear optical effects such as the multiphoton fluorescent imaging, the CARS imaging or the like, the conversion efficiency from excitation light to signal light is essentially low, and thus the optical signals obtained from an organism are significantly weak. Therefore, it is difficult to obtain a clear image.

As a method of solving this problem, it is conceivable that the intensity of excitation light with which an organism is irradiated is rendered to be higher. However, when an organism is irradiated with light having excessively high intensity, it could be possible to damage the organism. Thus, the intensity of excitation light has an upper limit. Therefore, it is difficult to obtain a clear image in lots of cases.

Then, it is general that a low-noise high-sensitivity photodetector is used to obtain a clearer image.

As the currently-used typical photodetection device, there can be mentioned PMT (Photo multiplier tube), APD (Avalanche photo diode) and PD (Photo diode). The PMT and the APD perform electron multiplying in the detection device, which enables high-sensitive photodetection. On the other hand, the PD does not have an electron multiplying function in the detection device and thus signals are usually amplified with the use of an electric amplifier, although it achieves a very high response speed. That is, any devices of PMT, APD and PD perform signal amplification in an electric domain to improve the sensitivity.

Moreover, there can be mentioned, as the typical two-dimensional photodetectors, CCD (Charged coupled device), CMOS (complementary metal Oxide semiconductor), EM-CCD (Electron multiplying-CCD), EB-CCD (Electron bombardment-CCD) and I-CCD (Intensified-CCD). When weak light is detected using the CCD or the CMOS, it is necessary, like the PD, to dispose an electric amplifier in a subsequent part so as to improve the sensitivity. The EM-CCD and the EB-CCD have an electron multiplying function in the detection device, like the APD, and achieve the higher sensitivity. The I-CCD has a configuration in which an Image intensifier (hereinafter referred to as I.I.) is disposed before the CCD. In the I.I, incident light signals are converted to electrical signals once, and electron multiplying is performed in a MCP (Micro channel plate) embedded in the I.I., thereafter the multiplied electrons are rendered to collide with a fluorescent plate so that the multiplied electrical signals are converted to light again. That is, the I-CCD also performs signal multiplying in an electric domain, achieving high-sensitive photodetection.

However, the low-noise and high-sensitivity photodetector is of particular and very expensive. Moreover, in the above conventional photodetection technique using signal amplification in an electric domain, the volume of noises generated from a photodetector and accumulated time of signal light by the photodetector have the inverse relationship, that is, the trade-off relationship therebetween, which requires sufficiently long accumulated time to obtain low-noise detection signals. As a result, sufficiently long accumulated time is needed to obtain a clear image after detecting weak signal light, thus extending time for obtaining an image. Therefore, real-time properties lack for needs to properly observe an organism varying with time, and it could be possible to inhibit basic needs by optical imaging users. Therefore, it is unavoidable in the present situation that either of detection speed or detection sensitivity is sacrificed to perform photodetection.

It is noted that such problem occurs not only in optical imaging methods but also in optical measuring methods such as the flow site meter optically analyzing fine particles in fluid, the fluorescence correlation spectroscopy (FCS) optically analyzing motion of fluorescently-labeled biomolecules in solution, the surface plasmon resonance method (SPR) optically analyzing the state of connection among biologically-relevant molecules fixed on the surface of a solid substrate and the latex photometric immunoassay (LPIA) optically analyzing the state of connection among biologically-relevant molecules in solution and the fluoroimmunoassay (FIA) detecting immune response in solution based on the existence or nonexistence of fluorescent label.

On the other hand, it has been conventionally active in development of the optical amplifier using optical fibers as the light transmission means mainly in the field of long-distance optical communication. As compared with the electric amplifier, the optical amplifier is capable of very high-speed wide-bandwidth operation and has properties, depending on the configuration, capable of low-noise and high-gain optical amplification. Such an optical amplifier is disposed before a high-speed photoelectric conversion device, thereby high-speed and high-sensitive photodetection can be expected (see Patent Document 1, for example).

The summary of Patent Document 1 is that optical irradiation is conducted by one of two optical fibers disposed at a given angle and the other performs photodetection, thereby the axial resolution in a depth direction of an object to be observed is improved.

Moreover, Amplified spontaneous emission (ASE) is generated from the optical amplifier, which is a dominant cause of noises in photodetection using the optical amplifier. Therefore, for achieving high-speed and high-sensitive photodetection using the optical amplifier, it is necessary that the optical amplifier is of low noise. With respect to the optical amplifier, as the light intensity of input signals becomes higher, the signal to noise ratio (hereinafter referred to as the SNR) after optical amplification is improved and thus the photodetection sensitivity is improved.

Moreover, a low-noise optical amplifier used in the field of long-distance optical communication is constituted by a single-mode optical fiber. The reasons why such a constitution by single-mode optical fiber is used are because the consistency with a transmission path is excellent and noises of the optical amplifier increase in proportion to a transmission mode of a gain fiber constituting the optical amplifier. Thus, in the field of long-distance optical communication, the use of a single-mode optical fiber as a gain fiber contributes greatly to low-noise properties of the optical amplifier.

However, even such a low-noise optical amplifier for long-distance optical communication constituted by a single-mode optical fiber has the following problem when used before a photoelectric conversion device. That is, it is often the case that signal light detected in the fields of organism observation, a sensor, security, laser radar and the like is scattered light or light with distorted wavefront. Such light has significantly low coupling efficiency to a single-mode optical fiber, and the light signal which can be taken in the optical amplifier is weak signals being of limited one portion of the whole. Therefore, the SNR is deteriorated and thus the high light-receiving sensitivity cannot be obtained.

On the other hand, it is conceivable that a multimode optical fiber amplifier having a large core diameter is disposed just before the photoelectric conversion device since it collects scattered light and light with distorted wavefront with high efficiency. However, since optical noises generated in the optical amplifier increase in accordance with the increase of the number of spatial modes resulted by increasing the core diameter, the SNR deteriorates in this case also and thus the high light-receiving sensitivity cannot be obtained.

Although the above is described with an example of a case in which light is detected, it is conceivable that cases in which electromagnetic waves other than light such as millimeter waves, microwaves and the like are detected also have the same problem.

On the other hand, there is conventionally known the organism tomographic image measuring technique using light referred as Optical coherence tomography (OCT) (see Non-Patent Document 5, for example). The OCT technique makes it possible to measure a tomographic image of an organism at a depth position of 1 mm to 2 mm, at resolution of about 1 μm to 10 μm.

The OCT technique is divided mainly to three methods of Time-domain (TD) OCT, Frequency-domain (FD) OCT (see Non-Patent Document 6, for example) and Swept source (SS) OCT (see Non-Patent Document 7, for example). Among them, the SSOCT using light whose wavelength varies with time enables measurement of an organism tomographic image at highest-speed and with highest-sensitivity, and the technical development thereof is being actively advanced.

However, the penetration depth of tomographic images obtained by OCT is presently about only 1 to 2 mm, and thus the performance is insufficient in diagnosis of penetration of cancer which is essential for early detection thereof. Thus, the applied range is limited.

The reason why the penetration depth by OCT is not improved is because optical signals returning from the deep portion of the organism to the surface thereof are weak due to light scattering effects or light absorbing effects in the organism and thus the signals from the deep portion are buried in noises such as shot noises, thermal noises, quantization noises and the like which are generated in the detection process. Particularly in the case of SSOCT, quantization noises (quantization errors) in an analog-digital converter (ADC) are the cause of limiting the penetration depth.

That is, in the SSOCT, analog signals after photoelectric conversion are of high frequency in a deep portion of an organism and of low frequency in a shallow portion thereof, and the signal from a shallow portion of the organism usually has higher intensity by several orders of magnitude than that from a deep portion thereof. Therefore, when such a signal is quantized by the ADC, high-frequency components with small amplitude having information from the deep portion of the organism are buried in quantization noises and information from the deep portion cannot be taken out even when an ADC having a relatively wide dynamic range of 14 bits is used, for example.

Patent Document 1: U.S. Pat. No. 6,423,956
Non Patent Document 1: W. Denk et al., Science 248, 73 (1990)
Non Patent Document 2: J. Jung and M. J. Schnitzer, Opt. Lett. 28, 902 (2003)
Non Patent Document 3: A. Zumbusch et al., Phys. Rev. Lett. 82, 4142 (1999)
Non Patent Document 4: I. Freund et al., Biophys. J. 50, 693 (1986)
Non Patent Document 5: D. Huang et al., Science 254, 1178 (1991)
Non Patent Document 6: R. Leitgeb et al., Opt. Lett. 25, 820 (2000)
Non Patent Document 7: S. R. Chinn et al., Opt. Lett. 22, 340 (1997)

DISCLOSURE OF THE INVENTION

Problems to be Solved by the Invention

Therefore, an object of the invention in view of the above aspects is to provide an optical inspection device capable of collecting low-noise detection signals with high efficiency with its inexpensive configuration even when signals to be detected transmitted from an object are weak without increasing the intensity of light with which the object to be observed is irradiated and without using an expensive low-noise and high-sensitivity photodetector. Moreover, an object of the invention is to provide an electromagnetic wave detection method, an electromagnetic wave detection device, and an organism observation method, a microscope and an endoscope capable of detecting electromagnetic waves at high speed and with high sensitivity even when the electromagnetic waves to be detected (signals to be detected) are scattered electromagnetic waves or electromagnetic waves with distorted wavefront due to an organism and the like.

Furthermore, an object of the invention is to provide an optical tomographic image generation device capable of converting information from a deep portion of an object to be inspected by SSOCT to digital signals with high accuracy without burying the information in quantization noises and of improving the penetration depth of a tomographic image.

SUMMARY OF THE INVENTION

The invention is based on a fundamental configuration in which detected signals or detected electromagnetic waves are amplified not in an electric domain but by a light amplification means or an electromagnetic wave amplification means before converting such signals from light or electromagnetic waves to electrical signals. Moreover, in a plurality of aspects of the invention, a mode adjustment means is provided before the amplification means to render the signal mode of detected signals or detected electromagnetic waves to be substantially equal to the amplification spatial mode of the amplification means. Furthermore, other plurality of aspects of the invention, the configuration of the optical inspection device using the light amplification means of the application is applied in an optical tomographic image generation device. The method for solving problems according to each aspect of the application will be described.

A first aspect of the invention relating to an optical inspection device for achieving the above object is an optical inspection device, comprising a light generation means, a light irradiation means irradiating an object to be inspected with light generated from the light generation means and a photodetection means photoelectrically converting signal light obtained from the object to be inspected through irradiation of light by the light irradiation means, and inspecting the object to be inspected based on output from the photodetection means, wherein a light amplification means amplifying signal light obtained from the object to be inspected is provided.

A second aspect of the invention is an optical inspection device according to the first aspect, wherein the light amplification means comprises a waveguide-type optical amplifier.

A third aspect of the invention is an optical inspection device according to the second aspect, wherein the waveguide-type optical amplifier is constituted by a semiconductor optical amplifier.

A fourth aspect of the invention is an optical inspection device according to the second aspect, wherein the waveguide-type optical amplifier is constituted by an optical fiber amplifier.

A fifth aspect of the invention is an optical inspection device according to any one of the first to fourth aspects, wherein the light amplification means amplifies, as the signal light, light having a wavelength different from that of light with which the object to be inspected is irradiated.

A sixth aspect of the invention is an optical inspection device according to the fifth aspect, wherein the light amplification means amplifies, as the signal light, fluorescence or phosphorescence generated from the object to be inspected.

A seventh aspect of the invention is an optical inspection device according to the fifth aspect, wherein the light amplification means amplifies, as the signal light, light generated by nonlinear optical effects in the object to be inspected.

An eighth aspect of the invention is an optical inspection device according to any one of the first to seventh aspects, comprising a gain control means controlling a gain of the light amplification means in synchronization with timing of incidence of the signal light on the light amplification means.

A ninth aspect of the invention is an optical inspection device according to any one of the first to eighth aspects, wherein the light amplification means is configured so that a wavelength region of light to be amplified is narrower than that of light to be incident.

A tenth aspect of the invention is an optical inspection device according to any one of the first to ninth aspects, wherein a back reflection prevention means preventing back reflection from the light amplification means to the object to be inspected is provided at the input side of the light amplification means.

An eleventh aspect of the invention is an optical inspection device according to any one of the first to tenth aspects, wherein a wavelength selection means selecting a wavelength of signal light to be photoelectrically converted by the photodetection means is provided between the light amplification means and the photodetection means.

A twelfth aspect of the invention is an optical inspection device according to any one of the first to eleventh aspects, comprising an optical system connecting the object to be inspected with the light amplification means in optical conjugation.

A thirteenth aspect of the invention is an optical inspection device according to any one of the first to twelfth aspects, wherein the object to be inspected is an organism; and the light amplification means amplifies, as the signal light, light modulated by the organism.

A fourteenth aspect of the invention is an optical inspection device according to any one of the first to thirteenth aspects, wherein the light generation means generates laser light.

A fifteenth aspect of the invention is an optical inspection device according to any one of the first to fourteenth aspects, comprising an image display means displaying an image based on output from the photodetection means, wherein the light irradiation means comprises a light scan means scanning with light with which the object to be inspected is irradiated in at least two-dimensional direction; and an image of an area of the object to be inspected scanned by the light scan means is displayed on the image display means based on output from the photodetection means.

A sixteenth aspect of the invention relating to an electromagnetic wave detection device for achieving the above object is an electromagnetic wave detection device, comprising a mode adjustment means adjusting a mode condition of incident multimode electromagnetic waves;

an amplification means amplifying the electromagnetic waves in which the mode condition has been adjusted output from the mode adjustment means; and a conversion means converting the amplified electromagnetic waves output from the amplification means to electrical signals, wherein the mode adjustment means is configured to adjust, by converting energy mode distribution, the incident multimode electromagnetic waves to of a mode substantially equal to an amplification spatial mode by the amplification means.

A seventeenth aspect of the invention is an electromagnetic wave detection device according to the sixteenth aspect, wherein the mode adjustment means is configured to reduce the number of spatial modes of incident electromagnetic waves.

A eighteenth aspect of the invention is an electromagnetic wave detection device according to the sixteenth aspect, wherein the mode adjustment means is configured to vary an energy ratio among spatial modes of incident electromagnetic waves.

A nineteenth aspect of the invention is an electromagnetic wave detection device according to the sixteenth aspect, wherein the incident electromagnetic waves are light; and the mode adjustment means is constituted by an optical waveguide.

A twentieth aspect of the invention is an electromagnetic wave detection device according to the nineteenth aspect, wherein the optical waveguide is constituted by an optical fiber.

A twenty-first aspect of the invention is an electromagnetic wave detection device according to the twentieth aspect, wherein the optical fiber is constituted by a tapered optical fiber.

A twenty-second aspect of the invention is an electromagnetic wave detection device according to the nineteenth aspect, wherein the optical waveguide is constituted by a refractive-index distribution type waveguide having nonuniform refractive-index distribution in a longitudinal direction of the optical waveguide or configured to adjust the mode condition by applying nonuniform stress distribution or nonuniform temperature distribution in a longitudinal direction of the optical waveguide.

A twenty-third aspect of the invention is an electromagnetic wave detection device according to the sixteenth aspect, wherein the incident electromagnetic waves are light; and the amplification means is an optical fiber amplifier.

A twenty-fourth aspect of the invention is an electromagnetic wave detection device according to the twenty-third aspect, wherein the optical fiber amplifier is a rare-earth-doped optical fiber amplifier.

A twenty-fifth aspect of the invention is an electromagnetic wave detection device according to the twenty-fourth aspect, wherein the rare-earth-doped optical fiber amplifier is a rare-earth-doped fluoride optical fiber amplifier.

A twenty-sixth aspect of the invention is an electromagnetic wave detection device according to the twenty-third aspect, wherein the optical fiber amplifier is an optical fiber amplifier using stimulated Raman scattering effects.

A twenty-seventh aspect of the invention is an electromagnetic wave detection device according to the sixteenth aspect, wherein the incident electromagnetic waves are light; and the amplification means is a semiconductor optical amplifier.

A twenty-eighth aspect of the invention is an electromagnetic wave detection device according to the sixteenth aspect, wherein the incident electromagnetic waves are light; and the amplification means is an optical amplifier having dye.

A twenty-ninth aspect of the invention is an electromagnetic wave detection device according to the sixteenth aspect, wherein the amplification means varies a gain depending on timing of incidence of the incident electromagnetic waves.

A thirtieth aspect of the invention is an electromagnetic wave detection device according to the sixteenth aspect, wherein the electromagnetic wave detection means has, before the mode adjustment means, a collecting means collecting the incident electromagnetic waves and causing them to be incident on the mode adjustment means.

A thirty-first aspect of the invention is an electromagnetic wave detection device according to the sixteenth aspect, wherein the electromagnetic wave detection means has, before the mode adjustment means, a plurality of collecting means collecting the incident electromagnetic waves in parallel and causing them to be incident on the mode adjustment means.

A thirty-second aspect of the invention is an electromagnetic wave detection device according to the thirty-first aspect, comprising a multiplex means multiplexing a plurality of electromagnetic waves output from the plurality of collecting means, wherein electromagnetic waves output from the multiplex means are input to the mode adjustment means.

A thirty-third aspect of the invention relating to an electromagnetic wave detection device for achieving the above object is an electromagnetic wave detection device, comprising a plurality of mode adjustment means respectively adjusting a mode condition of incident multimode electromagnetic waves which are incident in parallel;

a multiplex means multiplexing a plurality of electromagnetic waves in which the mode condition has been adjusted output from the plurality of mode adjustment means;

an amplification means amplifying electromagnetic waves in which the plurality of electromagnetic waves have been multiplexed output from the multiplex means; and a conversion means converting the amplified electromagnetic wave output from the amplification means to electrical signals, wherein the mode adjustment means is configured to adjust, by converting energy mode distribution, the incident multimode electromagnetic waves to of a mode substantially equal to an amplification spatial mode by the amplification means.

A thirty-fourth aspect of the invention relating to an electromagnetic wave detection device for achieving the above object is an electromagnetic wave detection device, comprising a plurality of mode adjustment means respectively adjusting a mode condition of incident multimode electromagnetic waves which are incident in parallel;

a plurality of amplification means amplifying the plurality of electromagnetic waves in which the mode condition has been adjusted output from each of the mode adjustment means; and a parallel conversion means converting the plurality of amplified electromagnetic waves output from each of the plurality of amplification means to electrical signals in parallel, wherein the mode adjustment means is configured to adjust, by converting energy mode distribution, the incident multimode electromagnetic waves to of a mode substantially equal to an amplification spatial mode by the amplification means.

A thirty-fifth aspect of the invention relating to an electromagnetic wave detection method for achieving the above object is an electromagnetic wave detection method, comprising a mode adjustment step for adjusting a mode condition of incident multimode electromagnetic waves;

an amplification step for amplifying the electromagnetic waves in which the mode condition has been adjusted; and a conversion step for converting the amplified electromagnetic waves to electrical signals, wherein the adjustment step adjusts, by converting energy mode distribution, the incident multimode electromagnetic waves to of a mode substantially equal to an amplification spatial mode in the amplification step.

A thirty-sixth aspect of the invention relating to an organism observation method for achieving the above object is an organism observation method, comprising an irradiation step for irradiating an organism with electromagnetic waves; and a detection step for detecting, with the electromagnetic wave detection device according to any one of claims 16 to 35, electromagnetic waves to be detected obtained from the organism through irradiation with the electromagnetic waves, wherein the organism is observed based on electrical signals obtained in the detection step.

A thirty-seventh aspect of the invention relating to a microscope for achieving the above object is a microscope detecting electromagnetic waves to be detected from an object to be observed, comprising the electromagnetic wave detection device according to any one of claims 16 to 35, wherein the electromagnetic wave detection device is configured to detect the electromagnetic waves to be detected from the object to be observed.

A thirty-eighth aspect of the invention relating to an endoscope for achieving the above object is an endoscope detecting electromagnetic waves to be detected from a body cavity and observing the inside of the body cavity, comprising the electromagnetic wave detection device according to any one of claims 16 to 35, wherein the electromagnetic wave detection device is configured to detect the electromagnetic waves to be detected from the body cavity.

A thirty-ninth aspect of the invention is an optical inspection device according to the first aspect, comprising an optical multiplex-demultiplex unit demultiplexing light from the light generation means to inspection light and reference light so that the object to be inspected is irradiated with the inspection light by the light irradiation means and the reference light is guided to a light reflection unit, amplifying, by the light amplification means, reflected inspection light obtained in a way that the inspection light is reflected and scattered by the object to be inspected, and multiplexing the amplified reflected inspection light and reflected reference light obtained in a way that the reference light is reflected by the light reflection unit so as to generate interference light;

an analog signal process unit attenuating low-frequency components of photoelectric conversion signals obtained from the photodetection means relative to high-frequency components thereof;

an analog-digital conversion unit converting analog output signals from the analog signal process unit to digital signals; and an image process unit processing digital output signals from the analog-digital conversion unit so as to generate an optical tomographic image, wherein the light generation means is a wavelength-variable light source unit emitting light whose wavelength varies with time; and the photodetection means is a photoelectrical conversion unit receiving interference light generated by the optical multiplex-demultiplex unit and photoelectrically converting the same.

A fortieth aspect of the invention is an optical inspection device according to the thirty-ninth aspect, wherein an optical filter removing optical noises is provided between the light amplification means and the optical multiplex-demultiplex unit.

A forty-first aspect of the invention is an optical inspection device according to the fortieth aspect, wherein the optical filter is constituted by a band-pass filter in which a transmitted central wavelength is variable; and the transmitted central wavelength is varied in synchronization with variation with time of wavelength of light emitted from the wavelength-variable light source unit.

A forty-second aspect of the invention relating to an optical tomographic image generation device for achieving the above object is an optical tomographic image generation device comprising the optical inspection device according to any one of claims 39 to 41.

EFFECT OF THE INVENTION

According to the invention, signal light obtained from an object to be inspected is amplified by a light amplification means and then photoelectrically converted by a photodetection means, which makes it possible to photoelectrically convert signal light from the object to be inspected with high sensitivity and promptly with its inexpensive configuration without increasing the intensity of light with which the object to be inspected is irradiated and without using an expensive low-noise and high-sensitivity photodetector as the photodetection means.

Figure 1:
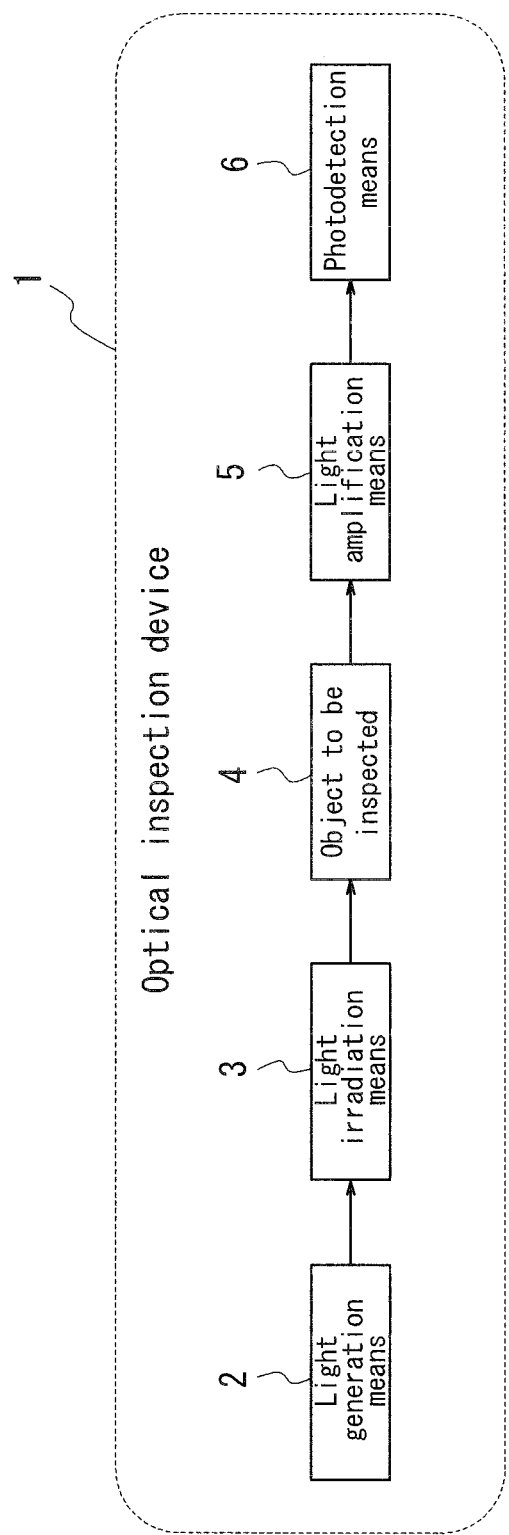
FIG. 1 is a functional block diagram illustrating a fundamental configuration of the optical inspection device of the invention.

REFERENCE SYMBOLS 1 optical inspection device
2 light generation means
3 light irradiation means
4 object to be inspected
5 light amplification means
6 photodetection means
11 fat
12 blood vessel
15 movable table
16 projector lens
17 collective lens
21 computer
22 movable table control device
25 single-mode optical fiber
26 laser diode (LD)
27 function generator
28 LD driver
31 multimode optical fiber
32 light amplification means
33 band-pass filter
34 photodetection means
35 transimpedance amplifier
36 lock-in amplifier
37 analog-digital (A/D) converter
38 monitor
41 excitation light source
42 multiplex device
43 rare-earth-doped optical fiber
44 excitation light removal device
45 optical isolator
46 optical isolator
47 Silica optical fiber
51 laser scanning confocal fluorescence microscope
52 He—Ne laser
53 light intensity adjustment device
54 dichroic mirror
55 X-Y galvano scanner mirror
56 pupil lens
57 tube lens
58 objective lens
60 living cell sample
61 optical isolator
62 collective lens
63 light amplification means
64 photomultiplier tube
65 computer
66 monitor
71 laser scanning multiphoton fluorescence microscope
72 Titanium-sapphire laser
73 gain control means
81 laser scanning CARS microscope
82 two-wavelength optical pulse source
83 living cell sample
84 band-pass filter
110 mode adjustment means
111 tapered fiber
111a core portion of tapered fiber
112 tapered waveguide
120 amplification means
121 Er-doped fluoride optical fiber amplifier
122 semiconductor optical amplifier (SOA)
123 semiconductor optical amplifier (SOA)
130 conversion means
131 PIN-PD
132 CCD camera
133 PIN-PD
140 multiplex means
141 fiber coupler
142 multimode fiber coupler
150 collecting means
151 collective lens
152 collective lens
161 Er-doped fluoride fiber laser
162 isolator
163 SMF
164a collimator
164b lens for lighting
165 scan mount
166 laser driver
167 electric amplifier
168 AD converter
169 computer
170 display monitor
171 driver
172 driver
173a isolator
173b isolator 174 WDM coupler
175 Er-doped fluoride fiber
176 optical filter
177 LD
178 housing
179 laser driver
180 LD
181 isolator
182a MMF
182b MMF
183 lens for lighting
184a isolator
184b isolator
185 BPF
186 driver
187 Titanium-sapphire laser
188 light intensity adjustment device
189 X-Y galvano scanner mirror
190 pupil lens
191 tube lens
192 dichroic mirror
193 objective lens
200 organism sample
201 living cell sample
202 isolator
203 gain control means
301 wavelength-variable light source unit
302 image process unit
303 wavelength control unit
305 optical multiplex-demultiplex unit
306 reference-side optical transmission unit
307 inspection-side optical transmission unit
308 lens
309 light reflection unit
310 lens
311 object to be inspected
312 photoelectric conversion unit
313 analog signal process unit
314 analog-digital (A/D) conversion unit
315 display unit
321 frequency domain mode synchronization laser (FDML)
322 image process unit
323 filter control unit
324 optical circulator
325 3 dB coupler
326 single-mode optical fiber (SMF)
327 polarization controller
328 lens
329 optical attenuator
330 reflective mirror
331 single-mode optical fiber (SMF)
332 lens
333 galvano scanner mirror
334 lens
335 object to be inspected
336 scanner driver
337 dual-balanced receiver
338 highpass filter (HPF)
339 amplifier
340 A/D conversion unit
341 monitor
345 3 dB coupler
346 3 dB coupler
347 optical circulator
348 optical circulator
351 optical amplifier
352 optical band-pass filter (BPF)
353 filter control unit

BEST MODE FOR CARRYING OUT THE INVENTION

First, before explaining embodiments of the invention, the fundamental configuration of the optical inspection device of the invention will be described.

FIG. 1 is a functional block diagram illustrating a fundamental configuration of the optical inspection device of the invention. The optical inspection device 1 has a light generation means 2, a light irradiation means 3, a light amplification means 5 and a photodetection means 6. The light generation means 2 generates light for obtaining signal light from an object to be inspected, and generates light having a given wavelength or light having a given wavelength region according to a type of inspection. The light irradiation means 3 irradiates an object to be inspected 4 with the light generated by the light generation means 2, thereby signal light is generated from the object to be inspected 4. Here, the signal light generated from the object to be inspected 4 through light irradiation therefor is transmitted light or reflected light of irradiated light, fluorescence or phosphorescence generated through excitation by irradiated light, or light generated by nonlinear optical effects, for example, according to a type of inspection.

The light amplification means 5 inputs signal light according to a type of inspection obtained from the object to be inspected 4, amplifies the input signal light and outputs it to the photodetection means 6. The photodetection means 6 receives the signal light amplified by the light amplification means 5 and photoelectrically converts it. The electrical signals photoelectrically converted by the photodetection means 6 are processed according to a type of inspection at a signal processing circuit which is not shown, thereby the object to be inspected is inspected.

As above, signal light obtained from the object to be inspected 4 is amplified by the light amplification means 5 and then photoelectrically converted by the photodetection means 6, which makes it possible to photoelectrically convert signal light with high sensitivity and promptly without increasing the intensity of light with which the object to be inspected 4 is irradiated and without using an expensive low-noise high-sensitivity photodetector even when signal light obtained from the object to be inspected 4 is weak.

Next, embodiments of the invention will be described with reference to the accompanying drawings.

First Embodiment

Figure 2:
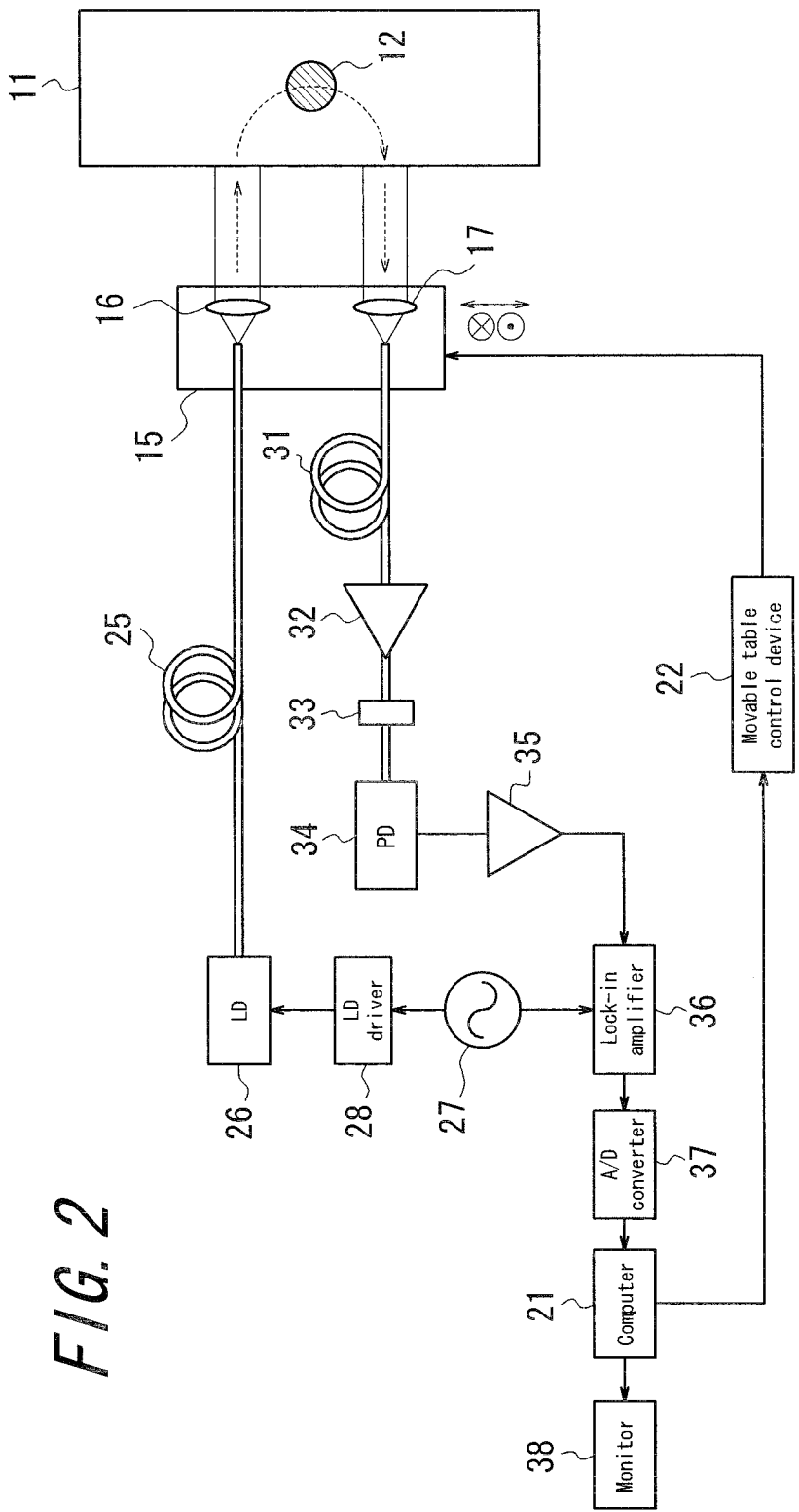
FIG. 2 is a functional block diagram illustrating a configuration of the optical inspection device according to the first embodiment of the invention.

FIG. 2 is a functional block diagram illustrating a configuration of the optical inspection device according to the first embodiment of the invention. The optical inspection device is a device for visualizing a route condition of a blood vessel 12 buried in fat 11 when a rigid endoscope is inserted to the inside of a body to approach organs like a stomach covered by fat. The device enables the scope-assisted surgery with avoiding bleeding due to wrong cutting of the blood vessel 12.

For this reason, the optical inspection device shown in FIG. 2 is provided, at a distal insertion portion of a rigid endoscope which is not shown, with a movable table 15 which can be moved in two-dimensional direction in a plane perpendicular to an insertion direction, and the movable table 15 is provided with a projector lens 16 for irradiating the object to be inspected with light and a collective lens 17 for collecting signal light from the object to be inspected at intervals of about 10 mm, for example. The computer 21 drives the movable table 15 in two-dimensional direction through a movable table control device 22 so that the movable table 15 scans with light with which the object to be inspected is irradiated. Therefore, in the embodiment, the movable table 15, the computer 21 and the movable table control device 22 constitute the light scan means.

The projector lens 16 is connected to a laser diode (LD) 26 as the light generation means via a single-mode optical fiber 25. As the laser diode 26, there is used one generating light having output of 50 mW, a spectral width of 1 nm and a central wavelength of 980 nm, for example. It is noted that light having a wavelength of 980 nm is low in optical absorptance at fat 11 of an organism and high in optical absorptance at hemoglobin in erythrocytes. An LD driver 28 drives the laser diode 26 based on sinusoidal modulation signals having a frequency of fm from a function generator 27. Thus, the laser diode 26 generates light intensity-modulated at a frequency of fm, and the intensity-modulated light is guided to the projector lens 16 via the single-mode optical fiber 25 to be rendered to a parallel beam by the projector lens 16, with which an organism is irradiated. In the optical inspection device, therefore, the single-mode optical fiber 25 and the projector lens 16 constitute the light irradiation means.

The light with which an organism is irradiated through the projector lens 16 is transmitted, reflected or scattered in fat 11, and when the blood vessel 12 runs in the fat 11, the light is absorbed by erythrocytes flowing therein and amplitude-modulated. As above, an organism is irradiated with light from the laser diode 26, thereby signal light obtained from the organism is collected by the collective lens 17 and the collected signal light is amplified by a light amplification means 32 via a multimode optical fiber 31. In the embodiment, the light amplification means 32 uses a waveguide-type optical amplifier such as a semiconductor optical amplifier, an optical fiber amplifier or the like, and is configured so as to have an amplification band of 3 nm and a gain of about 13 dB in a band having a wavelength of 980 nm, thereby the optical power of the received signal light is amplified to of about 20 times and the light is output.

The signal light amplified by the light amplification means 32 is received by a photodetection means (PD) 34 via a band-pass filter 33 and photoelectrically converted. As the band-pass filter 33, there is used of dielectric-multilayer-type having a central wavelength of 980 nm and a passband width of about 1 nm, for example. As a photodetection means 34, InGaAs/PIN photodiode is used, for example.

Outputs photoelectrically converted by the photodetection means 34 are converted to electric voltage by a transimpedance amplifier 35 and input in a lock-in amplifier 36. With sinusoidal modulation signals having a frequency of fm from the function generator 27 as reference signals, the lock-in amplifier 36 extracts voltage signals synthesized with the reference signals from input voltage signals from the transimpedance amplifier 35, The analog output signals extracted by the lock-in amplifier 36 are converted to digital signals by an analog-digital (A/D) converter 37 and provided to the computer 21.

The computer 21 processes digital signals of each point of an organism obtained from the A/D converter 37 through optical scanning by two-dimensional driving of the movable table 15, and displays an image on a monitor 38.

According to the embodiment, signal light from an organism collected by the collective lens 17 is amplified by the light amplification means 32 via the multimode optical fiber 31 and then photoelectrically converted by the photodetection means 34, which makes it possible to photoelectrically convert signal light with high sensitivity and promptly with constituting the photodetection means 34 by an inexpensive photodetector without increasing outputs of the laser diode 26 even when signal light obtained from an organism is weak. Then, there are obtained, from the lock-in amplifier 36, output voltage lower at scanned points where blood vessels run than at scanned points where blood vessels do not run within scanned area of the fat 11. Thus, it is possible to visualize the route of a blood vessel having a diameter of about 3 mm buried under fat having a thickness of 4 mm, for example. Therefore, an image displayed on the monitor 38 is observed, which enables the scope-assisted surgery with avoiding blood vessels, that is, with preventing bleeding due to cutting of blood vessels.

Figure 3:
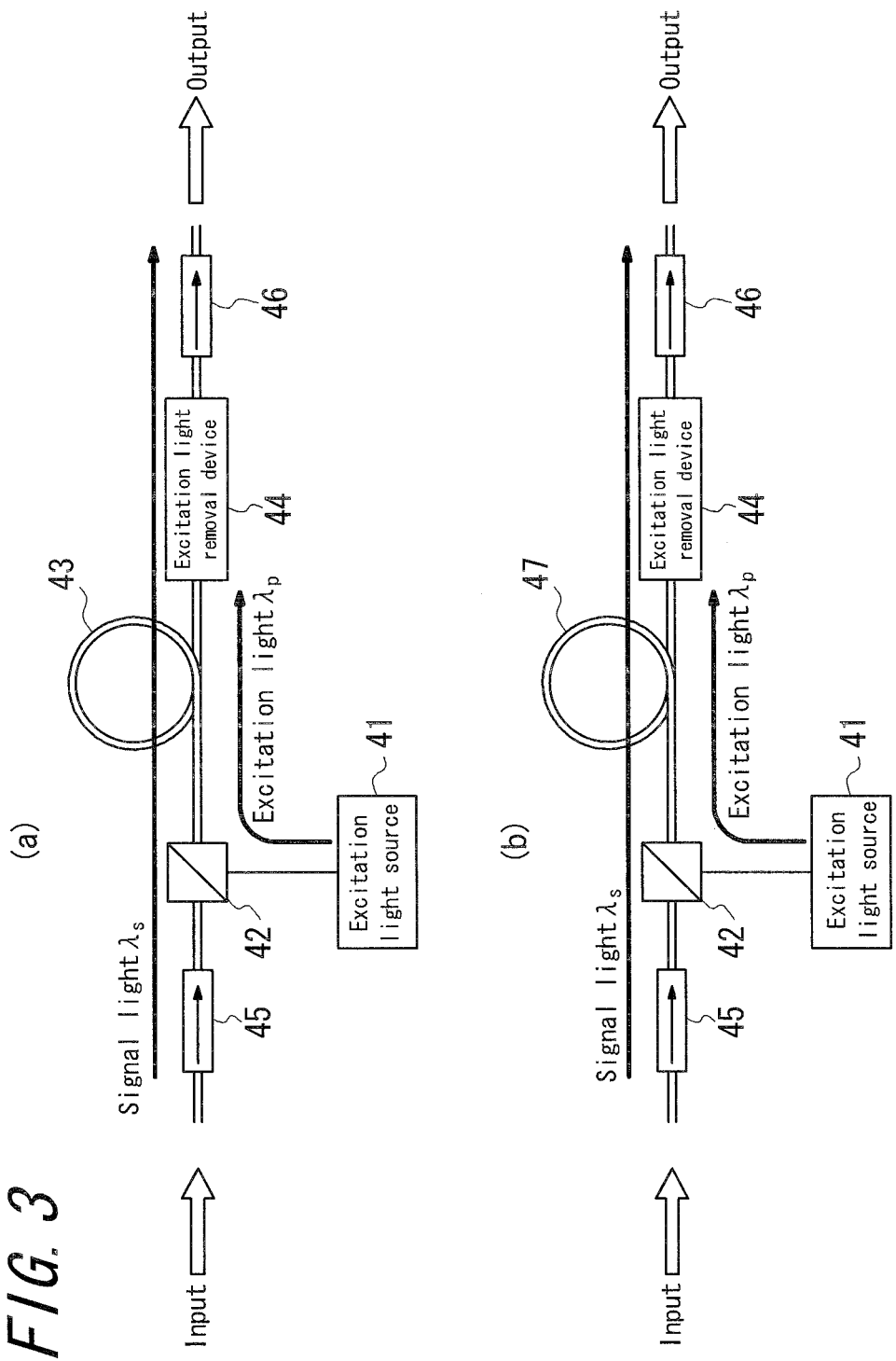
FIG. 3 is a diagram illustrating two examples of an optical fiber amplifier which can be used as the light amplification means shown in FIG. 2.

FIG. 3 is a diagram illustrating two examples of an optical fiber amplifier which can be used as the light amplification means 32 shown in FIG. 2. FIG. 3(a) illustrates a configuration of a rare-earth-doped optical fiber amplifier, and FIG. 3(b) illustrates a configuration of an optical Raman amplifier.

The rare-earth-doped optical fiber amplifier shown in FIG. 3(a) has an excitation light source 41, a multiplex device 42 such as a dichroic mirror or the like, a rare-earth-doped optical fiber 43 and an excitation light removal device 44, furthermore, it has optical isolators 45 and 46 at the input end and the output end respectively in order to prevent laser oscillation thereof. As the rare-earth-doped optical fiber 43, there is used one in which an optical fiber is doped with a rare earth such as Nd, Yb, Er, Tm, Pr or the like.

In FIG. 3(a), signal light having a wave length of $\lambda s$ input through the optical isolator 45 is multiplexed with excitation light having a wavelength of $\lambda p$ emitted from the excitation light source 41 at the multiplex device 42, and input into the rare-earth-doped optical fiber 43. Thus, the signal light is amplified using stimulated emission in the rare-earth-doped optical fiber 43 excited by excitation light. The output light from the rare-earth-doped optical fiber 43 is rendered to be incident on the excitation light removal device 44, in which residual excitation light is removed so that only signal light is transmitted. Thereafter, signal light having transmitted through the excitation light removal device 44 is output via the optical isolator 46.

When signal light having a wavelength of 980 nm is amplified by the rare-earth-doped optical fiber amplifier, as shown in FIG. 2, there is used, as each component, one having the following properties, for example. That is, as the excitation light source 41, there is used one having a wavelength of 915 nm, optical output of 50 mW and a spectral width of 1 nm. As the multiplex device 42, an optical fiber wavelength multiplex coupler is used. As the rare-earth-doped optical fiber 43, there is used a single clad multimode Yb-doped optical fiber or a single clad single-mode Yb-doped optical fiber having a length of 1 m and a low level of Yb added. The excitation light removal device 44 removes excitation light having a wavelength of 915 nm and uses a dielectric multilayer filter allowing signal light having a wavelength of 980 nm to pass therethrough. As the isolators 45 and 46, there are used ones having an operation wavelength of 980 nm, an isolation band of about 30 nm and return loss of 30 dB. Thus, it is possible to achieve a Yb-doped optical fiber amplifier for a wavelength band of 980 nm with low noise and high sensitivity.

With respect to the optical Raman amplifier shown in FIG. 3(b), in the configuration of the rare-earth-doped optical fiber amplifier shown in FIG. 3(a), a Silica optical fiber 47 is used instead of the rare-earth-doped optical fiber 43 and the Silica optical fiber 47 is excited by excitation light, thereby signal light is amplified using stimulated Raman scattering effects. The other configurations and operation are the same as in the rare-earth-doped optical fiber amplifier. Therefore, the same components are represented with the same reference symbols, and the description thereof will be omitted.

When signal light having a wavelength of 980 nm is amplified by the optical Raman amplifier, as shown in FIG. 2, there is used, as the excitation light source 41, one having a wavelength of 940 nm, optical output of 300 mW and a spectral width of 6 nm, for example. As the Silica optical fiber 47, there is used a multimode optical fiber or a single-mode optical fiber having a core diameter of 6 µm and a length of 2 km. The excitation light removal device 44 removes excitation light having a wavelength of 940 nm and uses a dielectric multilayer filter allowing signal light having a wavelength of 980 nm to pass therethrough. As the other components, there are used ones having properties described for the rare-earth-doped optical fiber amplifier shown in FIG. 3(a). Thus, it is possible to achieve an optical Raman amplifier for a wavelength of 980 nm with low noise and high sensitivity.

It is noted that, although the configurations shown in FIGS. 3(a) and 3(b) are of forward excitation so that excitation light is transmitted in the rare-earth-doped optical fiber 43 and the Silica optical fiber 47 in the same direction as signal light, they can be of backward excitation so that excitation light is transmitted in the opposite direction of signal light, or bidirectional excitation.

Second Embodiment

Figure 4:
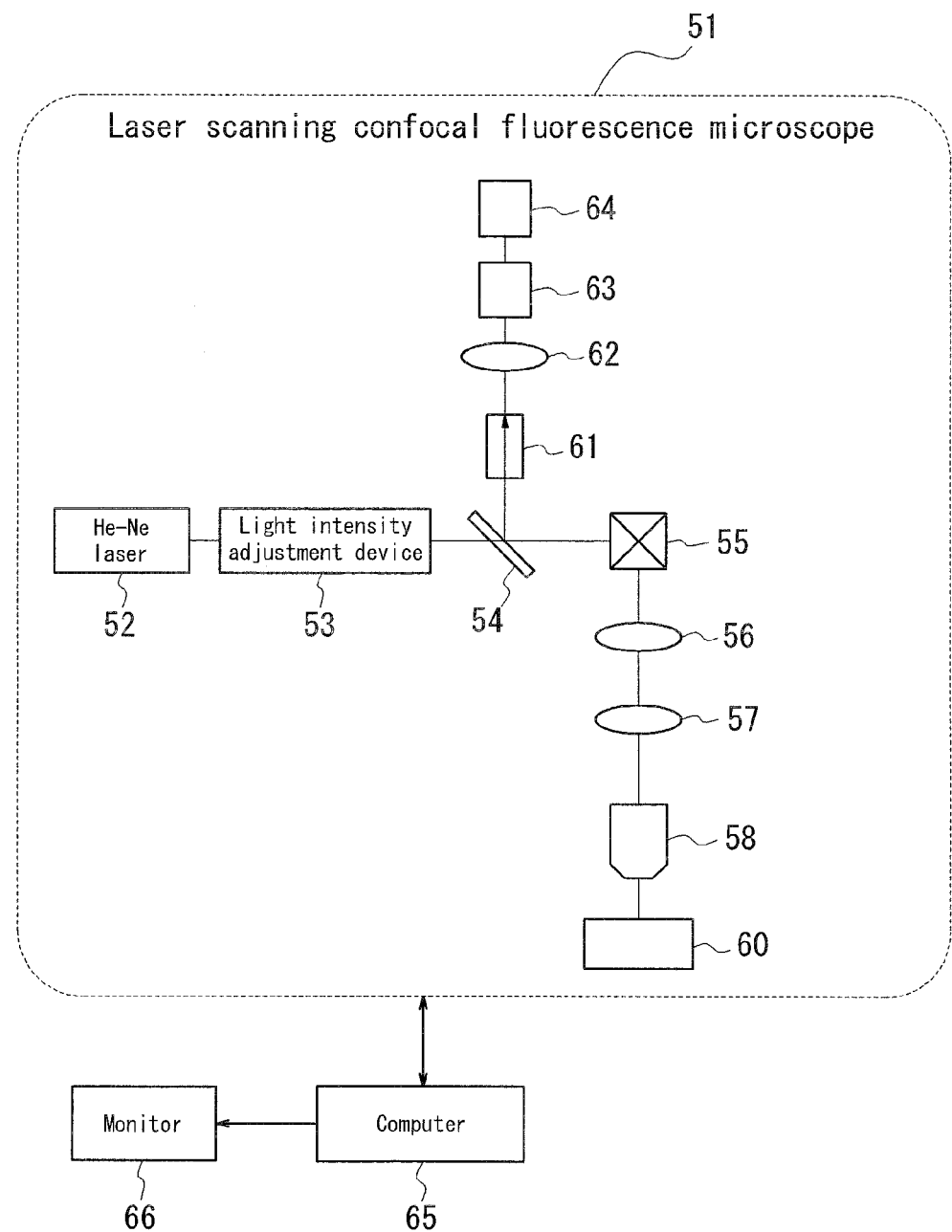
FIG. 4 is a functional block diagram illustrating a configuration of the optical inspection device according to the second embodiment of the invention.

FIG. 4 is a functional block diagram illustrating a configuration of the optical inspection device according to the second embodiment of the invention. In the embodiment, a laser scanning confocal fluorescence microscope 51 is constituted, and a He—Ne laser 52 continuously oscillating at a wavelength of 543 nm is provided as the light generation means. With respect to laser light emitted from the He—Ne laser 42, its light intensity is adjusted by a light intensity adjustment device 53 such as an acousto-optic modulator (AOM) or the like, for example. Then, the light passes through a dichroic mirror 54, an X-Y galvano scanner mirror 55, a pupil lens 56, a tube lens 57 and an objective lens 58, and is collected so that a living cell sample 60 to be inspected is irradiated therewith. Thus, in the laser scanning confocal fluorescence microscope 51, the light intensity adjustment device 53, the dichroic mirror 54, the X-Y galvano scanner mirror 55, the pupil lens 56, the tube lens 57 and the objective lens 58 constitute the light irradiation means. Moreover, the X-Y galvano scanner mirror 55 constitutes the light scan means.

It is noted that there is used, as the living cell sample 60, an object to be inspected dyed with fluorescent dye or an object to be inspected in which fluorescent protein is expressed. Here, an object to be inspected in which fluorescent protein DsRed is expressed, is used. Thus, when the living cell sample 60 is irradiated with laser light from the He—Ne laser 52, DsRed is excited and thus fluorescence having a wavelength of about 570 nm to 650 nm is generated.

The fluorescence generated from the living cell sample 60 passes through the objective lens 58, the tube lens 57, the pupil lens 56 and the X-Y galvano scanner mirror 55 to the dichroic mirror 54. The dichroic mirror 54 is configured so as to allow light having a wavelength of 543 nm to pass therethrough and so as to reflect light having a wavelength longer than 570 nm. Thereby, the fluorescence having a wavelength of about 570 nm to 650 nm generated in the living cell sample 60 is reflected by the dichroic mirror 54.

The fluorescence reflected by the dichroic mirror 54 passes through an optical isolator 61 and is collected by a collective lens 62, thereafter it is amplified by a light amplification means 63 having a semiconductor optical amplifier or an optical fiber amplifier. Then, the amplified fluorescence is received by a photomultiplier tube (PMT) 64 as the photodetection means and photoelectrically converted. The light amplification means 63 is configured so as to have a gain band having a gain of about 10 dB and a wavelength of 620 nm to 650 nm, for example.

The whole of laser scanning confocal fluorescence microscope 51 is controlled by a computer 65. Thus, laser light from the He—Ne laser 52 is deflected by the X-Y galvano scanner mirror 55, and the living cell sample 60 is two-dimensionally scanned in a plane perpendicular to a light axis from the objective lens 58. Then, the photoelectrically-converted output obtained from the photomultiplier tube 64 is processed at each scanned point to display a fluorescence image on a monitor 66.

According to the embodiment, fluorescence generated from the living cell sample 60 through irradiation with laser light from the He—Ne laser 52 is amplified by the light amplification means 63 and then photoelectrically converted by the photomultiplier tube 64, which makes it possible to photoelectrically convert fluorescence with high sensitivity and promptly with using the inexpensive photomultiplier tube 64 without increasing the intensity of laser light with which the living cell sample 60 is irradiated even when fluorescence as signal light obtained from the living cell sample 60 is weak.

In addition, the optical isolator 61 is disposed at the input side of the light amplification means 63, which can prevent back reflection to the living cell sample 60. Thereby, it is possible to prevent damages to the living cell sample 60 due to excessive light irradiation therefor and variation given to signal light. The reason will be described below. Generally, when light is amplified using an optical amplifier, it is unavoidable to add amplified spontaneous emission (ASE) noises. Thus, in the configuration of FIG. 4, it could be possible that one part of ASE generated at the light amplification means 63 is returned to the side of the living cell sample 60 and the excessive light irradiation damages the living cell sample 60 or varies signal light emitted from the living cell sample 60. In the embodiment, however, the optical isolator 61 is disposed at the incidence side of the light amplification means 63, which can prevent back reflection with ASE to the living cell sample 60 and thus prevent damages to the living cell sample 60 and variation of signal light therefrom.

Third Embodiment

Figure 5:
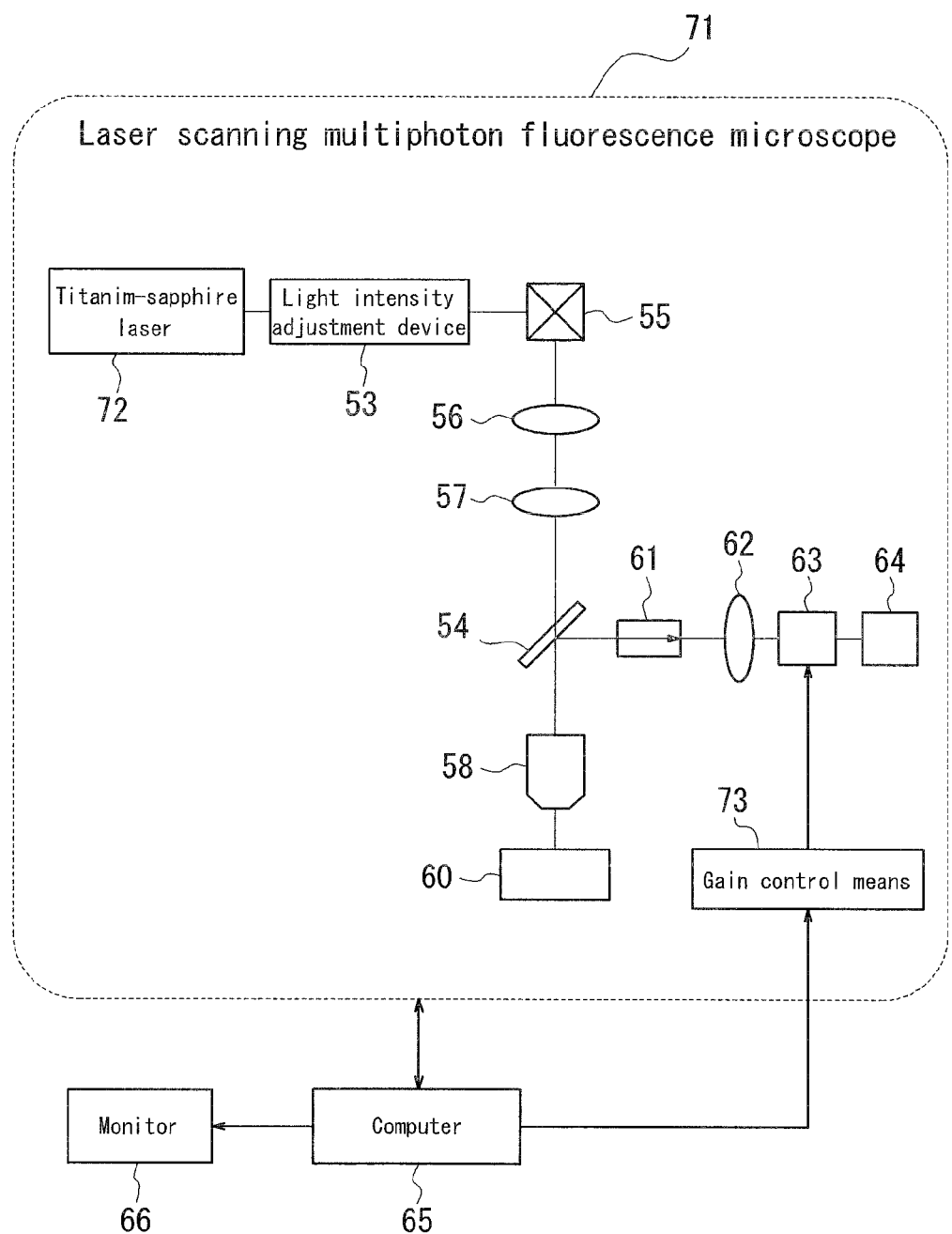
FIG. 5 is a functional block diagram illustrating a configuration of the optical inspection device according to the third embodiment of the invention.

FIG. 5 is a functional block diagram illustrating a configuration of the optical inspection device according to the third embodiment of the invention. In the embodiment, a laser scanning multiphoton fluorescence microscope 71 is constituted, and this embodiment is different, as compared with the configuration of the laser scanning confocal fluorescence microscope 51 shown in FIG. 4, mainly in aspects that a Titanium-sapphire laser 72 is used as the light generation means; the gain of the light amplification means 63 is controlled by the computer 65 through a gain control means 73; and the dichroic mirror 54 is disposed between the tube lens 57 and the objective lens 58 and its optical properties are rendered to be applied for the wavelength of emitted light from the Titanium-sapphire laser 72.

In the embodiment, ultrashort optical pulses having a repetition rate of 80 MHz, a pulse width of 150 fs and an oscillation wavelength of 1000 nm are generated from the Titanium-sapphire laser 72. With respect to the ultrashort optical pulses from the Titanium-sapphire laser 72, its optical average power is adjusted to 500 mW by the light intensity adjustment device 53. Then, the pulses pass through the X-Y galvano scanner mirror 55, the pupil lens 56, the tube lens 57, the dichroic mirror 54 and the objective lens 58, and are collected to irradiate the living cell sample 60 to be inspected therewith. Thereby, DsRed, for example, in the living cell sample 60 is multiphoton-excited (two-photon-excited, for example) to generate fluorescence.

The fluorescence generated from the living cell sample 60 passes through the objective lens 58 to the dichroic mirror 54. The dichroic mirror 54 is configured so as to allow light having a wavelength of 1000 nm from the Titanium-sapphire laser 72 to pass therethrough and so as to reflect light having a short wavelength of 700 nm or shorter. Thereby, fluorescence having a wavelength of about 570 nm to 650 nm generated in the living cell sample 60 is reflected by the dichroic mirror 54.

The fluorescence reflected by the dichroic minor 54 passes through the optical isolator 61, is collected by the collective lens 62 and amplified by the light amplification means 63, thereafter the amplified fluorescence is received by the photomultiplier tube 64 and photoelectrically converted.

Here, the fluorescence generated from the living cell sample 60 through two-photon excitation, for example, by excitation optical pulses from the Titanium-sapphire laser 72 lasts for about some nanoseconds. That is, the fluorescence generated from the living cell sample 60 becomes pulse light synchronized with excitation optical pulses from the Titanium-sapphire laser 72. Thus, in the embodiment, the computer 65 controls through the gain control means 73 so that, in synchronization with the timing at which this pulse form of fluorescence is incident on the light amplification means 63, the gain of the light amplification means 63 is increased at the timing of incidence of fluorescence.

The gain of the light amplification means 63 is controlled in a way that when a semiconductor optical amplifier is used, its driving current is increased or decreased or turned on or off, or in a way that when an optical fiber amplifier is used, the intensity of excitation light from an excitation light source is increased or decreased or the excitation light is turned on or off.

According to the embodiment, fluorescence generated from the living cell sample 60 through multiphoton excitation by excitation optical pulses from the Titanium-sapphire laser 72 is amplified by the light amplification means 63 and then photoelectrically converted by the photomultiplier tube 64, which makes it possible to photoelectrically convert fluorescence resulted by two-photon excitation with high sensitivity and promptly with using the inexpensive photomultiplier tube 64 without increasing the intensity of laser light with which the living cell sample 60 is irradiated even when fluorescence as signal light obtained from the living cell sample 60 is weak.

In addition, the gain of the light amplification means 63 is controlled in synchronization with the timing of incidence of fluorescence on the light amplification means 63, which can reduce the mixture of ASE noises during time in which fluorescence is not incident and thus improve the S/N.

Fourth Embodiment

Figure 6:
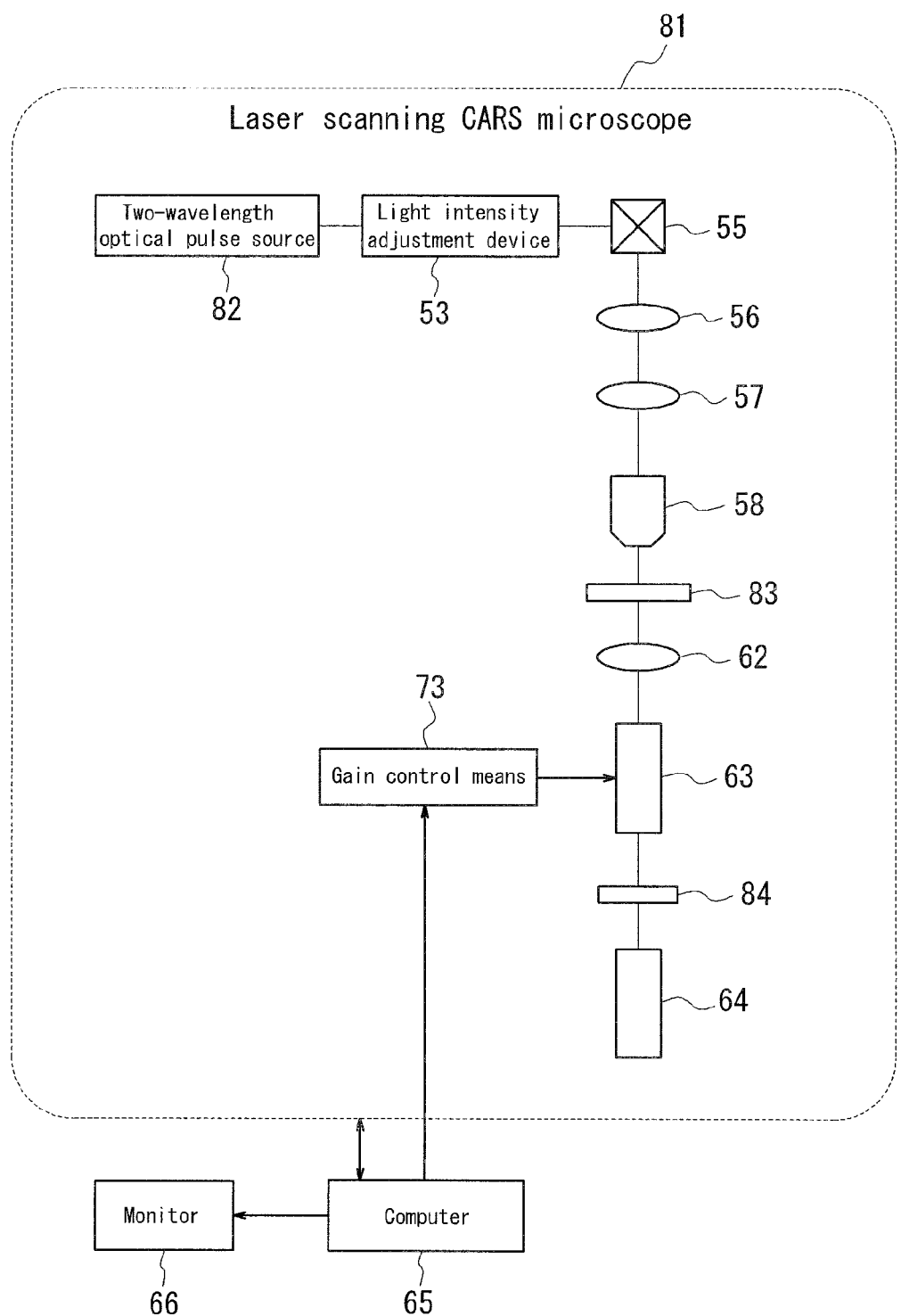
FIG. 6 is a functional block diagram illustrating a configuration of the optical inspection device according to the fourth embodiment of the invention.

FIG. 6 is a functional block diagram illustrating a configuration of the optical inspection device according to the fourth embodiment of the invention. In the embodiment, a laser scanning CARS microscope 81 is constituted, and a two-wavelength optical pulse source 82 is provided as the light generation means. The two-wavelength optical pulse source 82 is configured so as to generate light having a wave length of 1064 nm and 816 nm, for example, at a pulse width of about 5 ps and a repetition rate of 80 MHz, respectively. With respect to two-wavelength pulse light from the two-wavelength optical pulse source 82, its optical average power is adjusted to some tens of mW respectively by the light intensity adjustment device 53. Then, the light passes through the X-Y galvano scanner mirror 55, the pupil lens 56, the tube lens 57 and the objective lens 58 and is collected to irradiate a non-dyed living cell sample 83 to be inspected therewith. Thereby, CARS light is generated from the living cell sample 83.

The transmitted light including CARS light from the living cell sample 83 is collected by the collective lens 62 and amplified by the light amplification means 63, thereafter the output light is rendered to be incident on a band-pass filter 84 to extract CARS light having desired wavelength components. Then, the CARS light having passed through the band-pass filter 84 is received by the photomultiplier tube 64 and photoelectrically converted.

That is, in the embodiment, the transmitted light including CARS light from the living cell sample 83 is amplified by the light amplification means 63 having a gain band wider than the wavelength region of the CARS light, thereafter the band-pass filter 84 extracts CARS light having desired wavelength components and the photomultiplier tube 64 receives it. For example, when the wavelength of CARS light generated from the living cell sample 83 is about 660 nm, the light amplification means 63 is configured so as to have a gain band of wavelength from 650 nm to 670 nm and amplify transmitted light in such a gain band by 10 dB, for example, and the band-pass filter 84 is constituted by a dielectric multi layer filter having a central wavelength of 660 nm and a transmitted band width of about 10 nm. Moreover, CARS light generated from the living cell sample 83 is generated with the same repetition rate as of the excitation optical pulse train from the two-wavelength optical pulse source 82 and with duration of about some picoseconds. Thus, the computer 65 controls through the gain control means 73 so that, in synchronization with the timing at which CARS light is generated, the gain of the light amplification means 63 is increased at the timing of incidence of CARS light, in the same way as in the third embodiment.

The whole of laser scanning CARS microscope 81 is controlled by the computer 65, in the same way as in the third embodiment. Thereby, excitation pulses from the two-wavelength optical pulse source 82 are deflected by the X-Y galvano scanner mirror 55, and the living cell sample 60 is two-dimensionally scanned in a plane perpendicular to a light axis from the objective lens 58. Then, photoelectrically-converted output obtained from the photomultiplier tube 64 at each scanned point is processed so that a fluorescence image is displayed on the monitor 66.

According to the embodiment, CARS light generated from the non-dyed living cell sample 83 is amplified by the light amplification means 63 and then photoelectrically converted by the photomultiplier tube 64, which makes it possible to photoelectrically convert CARS light with high sensitivity and promptly with using the inexpensive photomultiplier tube 64 without increasing the intensity of laser light with which the living cell sample 83 is irradiated even when CARS light as signal light obtained from the living cell sample 83 is weak.

In addition, the band-pass filter 84 extracts CARS light having desired wavelength components from output light of the light amplification means 63, and the gain of the light amplification means 63 is controlled in synchronization with the timing of incidence of CARS light generated from the living cell sample 83, which makes it possible to remove undesired ASE noises which are within the gain band but out of desired wavelength region of the light amplification means 63 and thus improve the S/N.

Fifth Embodiment

Figure 7:
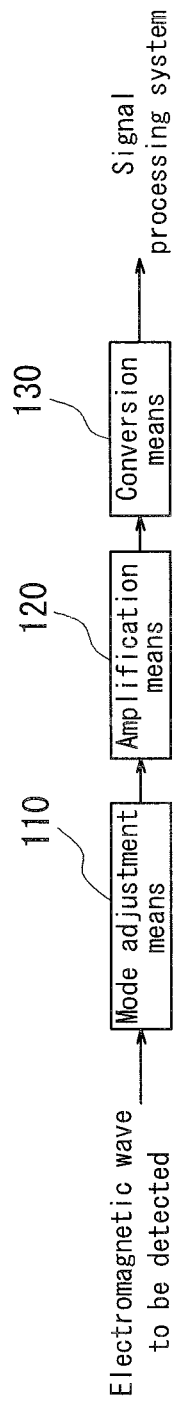
FIG. 7 is a block diagram illustrating a schematic configuration of the electromagnetic wave detection device according to the fifth embodiment of the invention.

FIG. 7 is a block diagram illustrating a schematic configuration of the electromagnetic wave detection device according to the fifth embodiment of the invention. The electromagnetic wave detection device amplifies electromagnetic waves to be detected emitted from a sample to be observed and provides them as electrical signals to a signal processing system. In the embodiment, since used for observing electromagnetic waves which are spontaneously emitted such as fluorescence and the like through bioluminescence, chemiluminescence and bioluminescence energy transfer, unlike the first to the fourth embodiments, the light generation means and the light irradiation means are not essential components.

The electromagnetic wave detection device according to the embodiment is provided with a mode adjustment means 110 adjusting the mode state of detected incident multimode electromagnetic waves, an amplification means 120 amplifying the electromagnetic waves whose mode state has been adjusted by the mode adjustment means 110 and a conversion means 130 converting the electromagnetic waves amplified by the amplification means 120 to electrical signals and outputting them to the signal processing system. The amplification means 120 has amplification properties excellent in the SNR for a specific amplification spatial mode, and the mode adjustment means 110 adjusts incident multimode electromagnetic waves to of a mode substantially equal to the amplification spatial mode by the amplification means 120 by converting the energy mode distribution.

Figure 8:
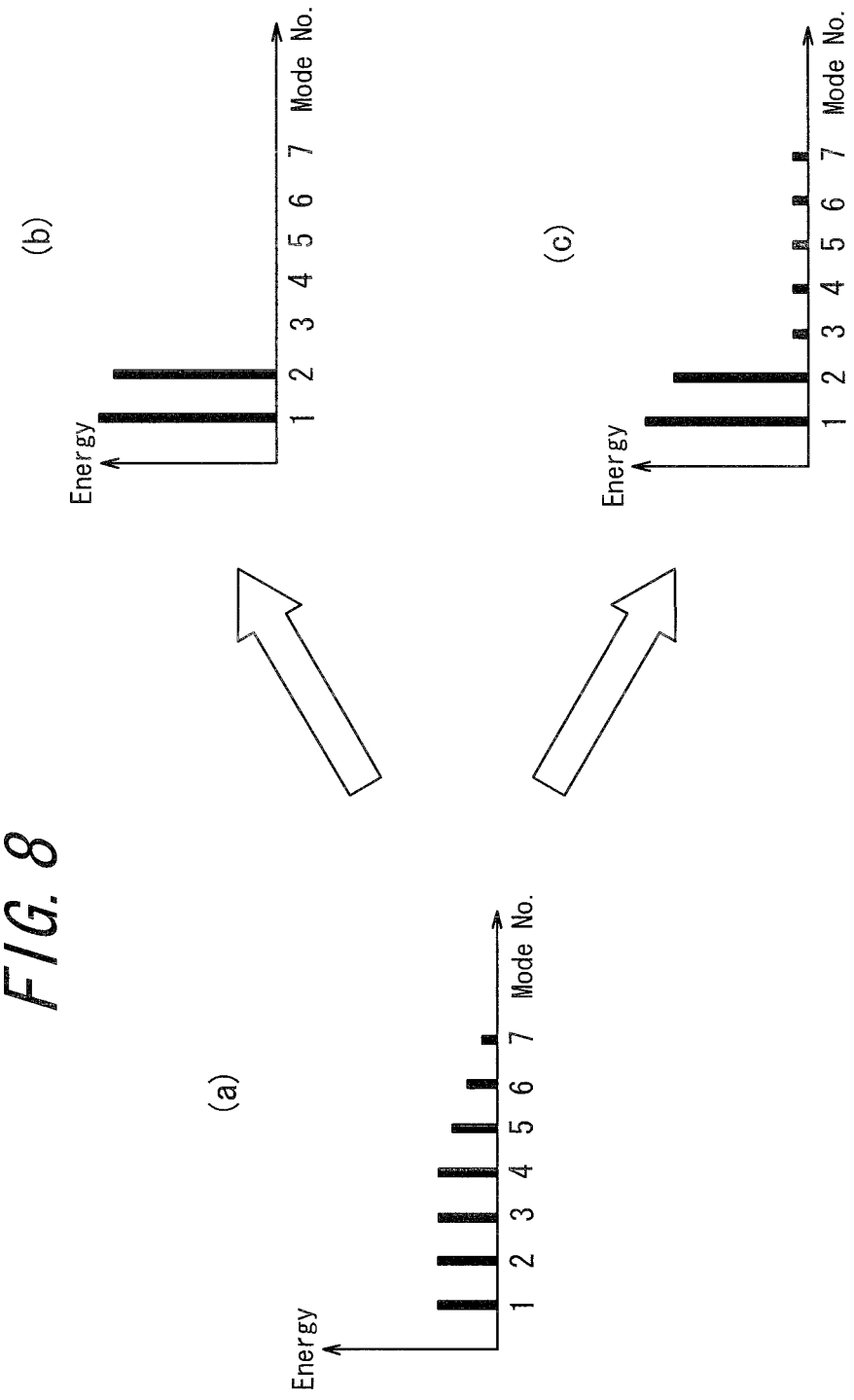
FIG. 8 is a diagram explaining mode adjustment by a mode adjustment means.

FIG. 8 is a diagram explaining mode adjustment by the mode adjustment means 110. The mode adjustment means 110 is configured so that incidence of multimode electromagnetic waves is allowed at the incidence side and, at the output side, adjustment is made to have the energy mode distribution substantially equal to of the amplification spatial mode of the subsequent amplification means 120, that is, the energy mode distribution with high consistency. FIG. 8(a) is an example of energy mode distribution of incident electromagnetic waves at the incidence side of the mode adjustment means. In this example, energy is distributed to a fundamental mode represented by the mode No. 1 and high-order modes represented by mode No. 2 to No. 7 FIGS. 8(b) and 8(c) are diagrams illustrating energy mode distribution of electromagnetic waves at the output side of the mode adjustment means 110 in different cases, respectively. In FIG. 8(b), the allowed mode is only two modes represented by mode No. 1 and No. 2, and energy in each mode at the incidence side of the mode adjustment means 110 is converted to these two modes with low loss. Moreover, FIG. 8(c) shows an example in which each of modes No. 1 to No. 7, which is the same for the incidence side, is allowed as energy mode distribution at the output side of the mode adjustment means but the distribution of two modes with mode No. 1 and No. 2 is significantly high because of the variation of energy mode distribution. That is, the number of spatial modes is artificially reduced in FIG. 8(c). The mode adjust means 110 may be either of one reducing the number of modes itself as in FIG. 8(b) or one varying the energy distribution as in FIG. 8(c).

With the schematic configuration of FIG. 7, electromagnetic waves to be detected which are scattered waves or waves with distorted wavefront are incident on the mode adjustment means 110 according to a mode allowed at the incidence side of the mode adjustment means 110. At that time, as a larger number of high-order modes are allowed, the coupling efficiency between detected electromagnetic waves and the mode adjustment means 110 becomes higher. Thereafter, the detected light is subjected to mode adjustment by the mode adjustment means 110 and emitted to the amplification means 120. Then, the mode distribution of energy of detected electromagnetic waves emitted from the mode adjust means 110 is substantially equal to the amplification spatial mode of the amplification means 120, which reduces energy loss due to inconsistency of the mode. Furthermore, the detected electromagnetic waves are amplified by the amplification means 120, emitted to the conversion means 130, and converted to electrical signals by the conversion means 130. The electrical signals output from the conversion means 130 are converted to desired data by the subsequent signal processing system.

According to the embodiment, as explained above, there is disposed the mode adjustment means 110 adjusting, by converting the energy mode distribution, incident multimode electromagnetic waves to of a mode substantially equal to the amplification spatial mode of the amplification means 120 before the amplification means and the conversion means, which makes it possible to collect detected electromagnetic waves with high efficiency even when they are scattered electromagnetic waves or electromagnetic waves with distorted wavefront, thus enabling high-speed high-sensitivity photodetection.

Sixth Embodiment

Figure 9:
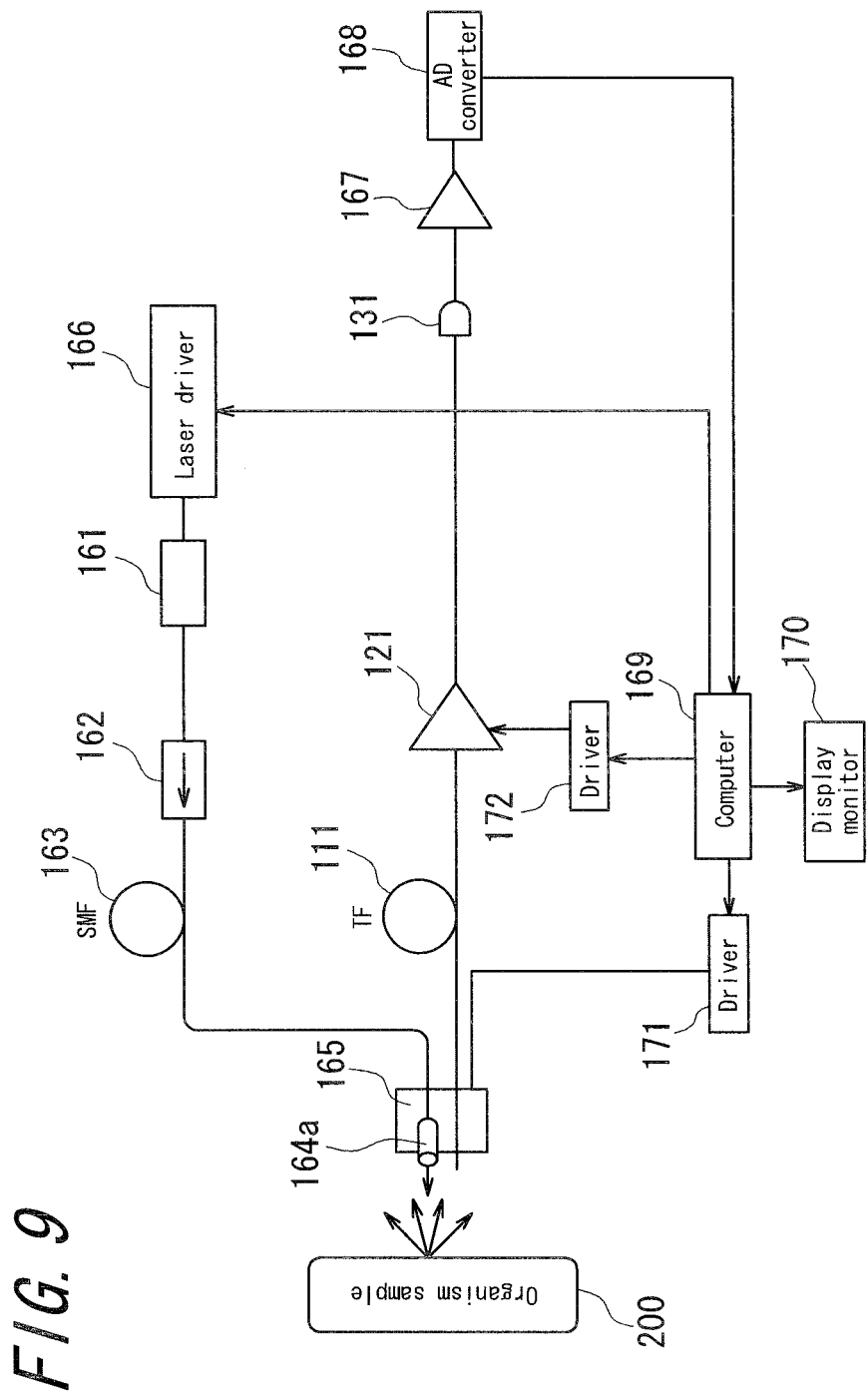
FIG. 9 is a diagram illustrating a schematic configuration of the rigid endoscope blood vessel imaging device according to the sixth embodiment of the invention.

FIG. 9 is a diagram illustrating a schematic configuration of the rigid endoscope blood vessel imaging device according to the sixth embodiment of the invention. The device detects signal light to be detected obtained by irradiation with laser light and visualizes the position of blood vessels existent under fat.

The rigid endoscope blood vessel imaging device is configured so that an organism sample 200 is irradiated with laser light for lighting while being scanned, and light reflected or scattered in the surface and the inside of the organism sample 200 is detected by the electromagnetic wave detection device having the configuration shown in FIG. 7 and converted to electrical signals, thereafter the electrical signals are processed by the signal processing system to display an image.

The rigid endoscope blood vessel imaging device is provided, as the lightning optical system, with a single-mode fiber (SMF) outputting Er-doped fluoride fiber laser 161 having a wavelength of 543 nm and output of 2 mW, an isolator 162, a single-mode fiber (SMF) 163 and a collimator 164, and is configured so that the desired observation position of the organism sample 200 is irradiated with laser light emitted from the Er-doped fluoride fiber laser 161 as a substantially-parallel beam through the collimator 164 via the isolator 162 and the SMF 163.

Furthermore, a laser driver 166 driving the Er-doped fluoride fiber laser 161 is provided, and the Er-doped fluoride fiber laser 161 is configured so that its output condition is controlled through the laser driver 166, by the computer 169 to be described controlling the whole of rigid endoscope blood vessel imaging device.

Moreover, in order to detect signal light from the organism sample 200, the rigid endoscope blood vessel imaging device shown in FIG. 9 is provided, as components corresponding respectively to the mode adjustment means 110, the amplification means 120 and the conversion means 130 in the electromagnetic wave detection device shown in FIG. 7, with a tapered fiber 111, an Er-doped fluoride optical fiber amplifier 121 and a silicon PIN-PD (PIN photo diode) 131. Furthermore, there are provided, after PIN-PD 131, an electric amplifier 167 amplifying electrical signals output from the PIN-PD 131 and an analog-to-digital (AD) converter 168 converting analog electrical signals amplified by the electric amplifier 167 to digital signals.

Figure 10:
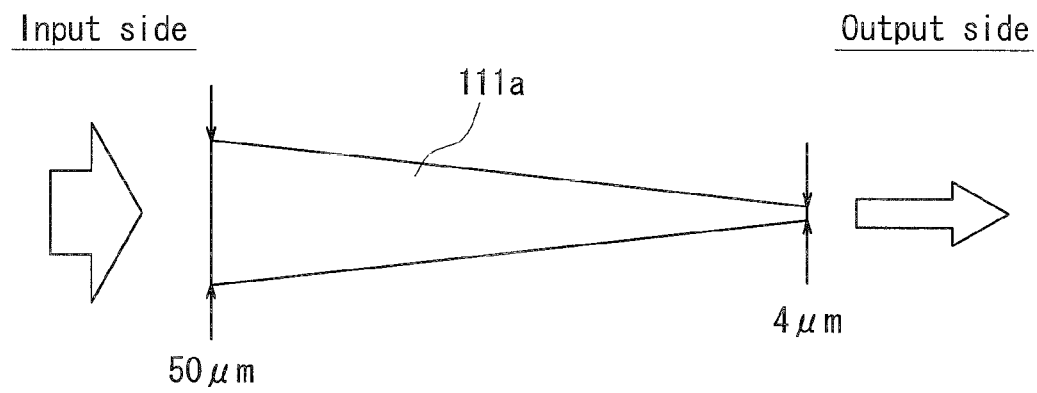
FIG. 10 is a diagram illustrating a schematic shape of a longitudinal section of a core portion of a tapered fiber.

The tapered fiber is an optical fiber having a configuration in which the diameter of core portion where light is waveguided is varied from the input side to the output side. The incidence surface of the tapered fiber 111 is disposed at a position front onto the organism sample 200 and adjacent to the collimator 164 and fixed, together with the collimator 164, on a scan mount 165. As FIG. 10 shows a schematic shape of a longitudinal section of the core portion, the tapered fiber 111 is of tapered form with a core diameter at the input side being larger than that at the output side. In the embodiment, there is used one with a core diameter at the input side and the output side being 50 µm and 4 µm respectively and a length being 1.0 m.

Figure 11:
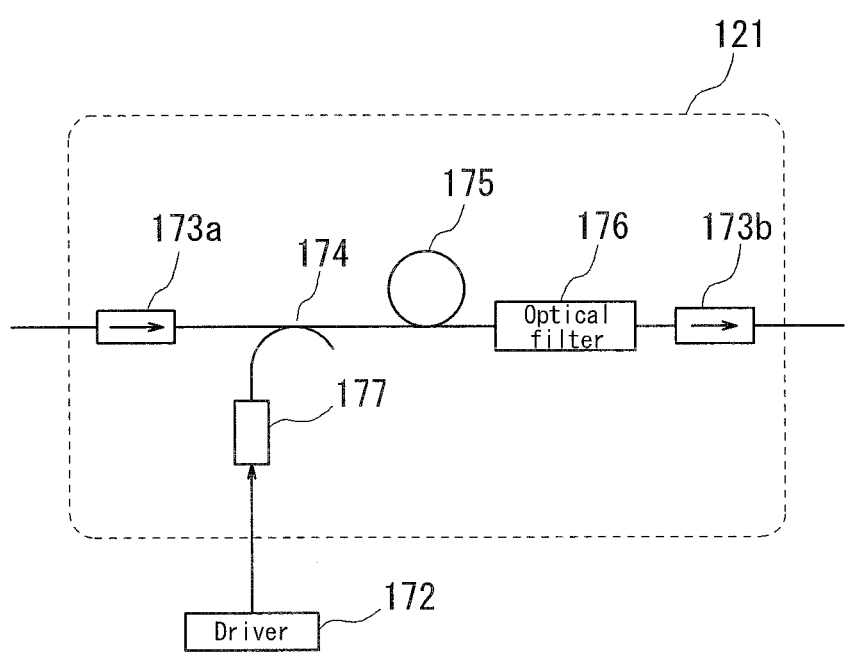
FIG. 11 is a schematic configuration diagram illustrating an Er-doped fluoride optical fiber amplifier.

The Er-doped fluoride optical fiber amplifier 121 is configured including isolators 173a, 173b, a wavelength divisional multiplexing (WDM) coupler 174, an Er-doped fluoride fiber 175, an optical filter 176 and a laser diode (LD) 177, as FIG. 11 shows its configuration diagram.

The isolators 173a and 173b are disposed at the input side and the output side of the Er-doped fluoride optical fiber amplifier 121 to block back reflection. The LD 177 is excitation light source of the Er-doped fluoride fiber 175, and a laser diode having a wavelength of 975 nm and output of 100 mW is used. Moreover, a driver 172 connected to the LD 177 and driving it is provided. The WDM coupler 174 is configured so as to multiplex excitation light from the LD 177 and signal light emitted from the isolator 173a at the incidence side and output it to the Er-doped fluoride fiber 175. The Er-doped fluoride fiber 175 is a single-mode Er-doped fluoride fiber having a core diameter of 4 µm, and it amplifies signal light by excitation light and outputs residual excitation light and ASE. The optical amplifier 176 is provided at the output side of the Er-doped fluoride fiber 175, and it removes residual excitation light and ASE to emit only signal light. The signal light is emitted from the Er-doped fluoride optical fiber amplifier 121 through the isolator 173b. The Er-doped fluoride optical fiber amplifier 121 can amplify output of the tapered fiber 111 by about 15 dB.

Moreover, the rigid endoscope blood vessel imaging device of the embodiment has a computer 169 controlling each unit of the device and processing digital signals output from an AD converter 168, as shown in FIG. 9. The computer 169 is connected to the laser driver 166, the driver 171 and the driver 172 to control the Er-doped fluoride fiber laser 161, the Er-doped fluoride optical fiber amplifier 121 and the scan mount 165 respectively, and is configured to perform signal processing with associating output signals of the AD converter 168 with each information of output of the Er-doped fluoride fiber laser 161, the gain of the Er-doped fluoride optical fiber amplifier 121 and the position of the scan mount 165 and display the result on a display monitor 170.

With the above configuration, when the rigid endoscope blood vessel imaging device of the embodiment is used in observing an organism sample, the computer 169 causes the scan mount 165 to scan through the driver 171, and drives the Er-doped fluoride fiber laser 161 through the laser driver 166 so that the organism sample 200 is irradiated with laser light from the collimator 164. The laser light is reflected or scattered in the surface and the inside of the organism sample 200 and incident on the tapered fiber 111 as signal light having a wavelength of 543 nm.

Here, since the core diameter at the incidence side of the tapered fiber 111 is 50 µm, as compared with a fiber having a core diameter of 4 µm, the area of incidence surface is larger and a spatially wider range of signals can be collected, and a large number of other high-order modes in addition to the fundamental mode can be incident. At the output side of the tapered fiber, on the other hand, the core diameter is as small as 4 µm, and thus the energy distribution among modes is adjusted and concentrated to the fundamental mode.

The signal light whose mode has been adjusted is incident on the Er-doped fluoride optical fiber amplifier 121 and then on the single-mode Er-doped fluoride fiber 175, shown in FIG. 11, having a fundamental mode as the amplification spatial mode and a core diameter of 4 µm. Since the mode distribution at the output side of the tapered fiber is substantially equal to the amplification spatial mode of the Er-doped fluoride fiber 175, the coupling efficiency at the combining portion thereof is higher. Thus, energy loss of signal light incident on the tapered fiber 111 can be minimized and amplification can be performed in a substantially-single mode at the Er-doped fluoride optical fiber amplifier 121, which makes it possible to suppress generation of ASE and thus obtain signal light having the high SNR.

Furthermore, signal light emitted from the Er-doped fluoride optical fiber amplifier 121 is converted to electrical signals by the PIN-PD 131, amplified by the electric amplifier 167, converted to digital signals by the AD converter 168 and transmitted to the computer 169, as shown in FIG. 9. The computer 169 performs signal processing with associating the electrical signals with information of scanned position and the like obtained from the driver 171 to generate a blood vessel image, and displays it on the monitor 170. Thus, it becomes possible to image the position of blood vessels existent under fat at high speed.

According to the embodiment, as explained above, the tapered fiber 111 is disposed before the Er-doped fluoride optical fiber amplifier 121, which can expand a light receiving surface and, further, since the number of spatial modes allowed at the incidence side is large, lots of signal light to be detected can be incident even if it is scattered light or light with distorted wavefront. Moreover, the tapered fiber 111 converts energy mode distribution to of a mode substantially equal to the amplification spatial mode of the Er-doped fluoride optical fiber amplifier 121 having a small number of amplification spatial modes, which can reduce ASE, thus enabling optical amplification with high SNR. Furthermore, the use of the tapered fiber 111 enables mode adjustment with small energy losses. Therefore, the optical amplification in which the light intensity of signals is high but the light intensity of noises is low is enabled even when detected signal light is scattered light or light with distorted wavefront. Therefore, the optical amplifier is disposed before the PIN-PD 131, which enables photodetection at high speed and with high sensitivity.

Moreover, the tapered fiber 111, which is one kind of optical fibers, is used as the mode adjustment means 110, which stably achieves a long spatial-mode-adjustment waveguide. When the waveguide is longer, it becomes possible to adjust spatial mode adiabatically, thus enabling the spatial mode adjustment with smaller loss. Moreover, the use of the optical fiber makes fine adjustment of spatial optical system unnecessary, thus improving the degree of freedom in use. Furthermore, with respect to the tapered fiber 111, the degree of freedom for its design is significantly high, which enables the mode adjustment means suitable for the condition of light to be detected. Moreover, the tapered fiber 111 can be produced relatively easily, which makes it possible to provide a low-cost photodetection device.

Moreover, there is used, as the amplification means 120, the Er-doped fluoride optical fiber amplifier 121, which enables amplification having the high amplification efficiency with high gain and low noise. Furthermore, the optical amplification is enabled in wavelength regions where no operation is possible with the Silica optical fiber amplifier and, in particular, the efficient optical amplification in visible bands becomes possible.

Seventh Embodiment

Figure 12:
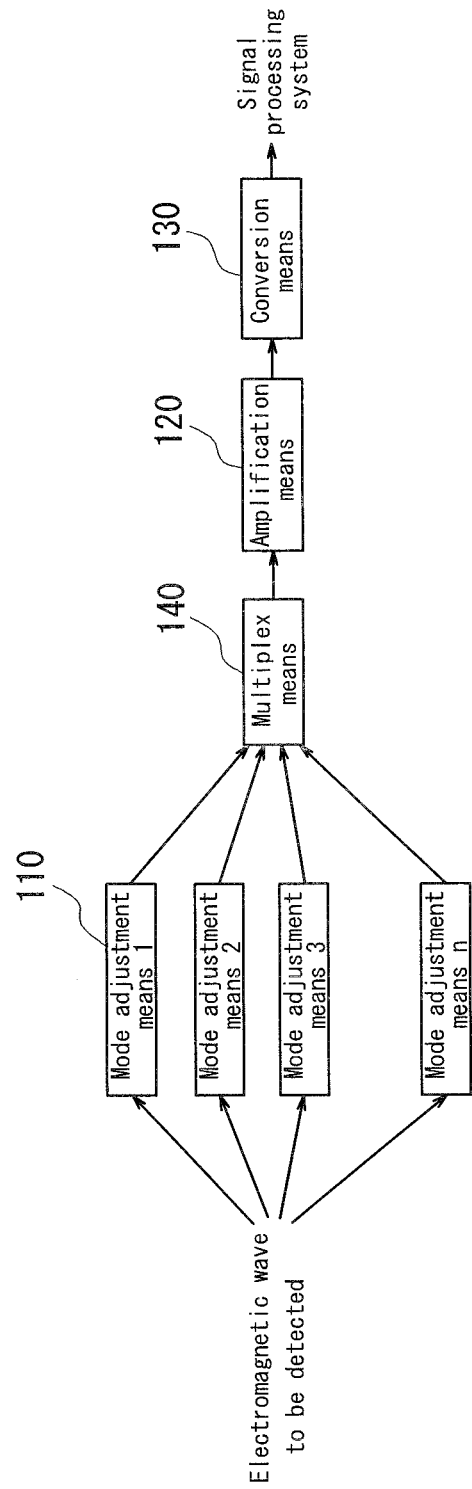
FIG. 12 is a block diagram illustrating a schematic configuration of the electromagnetic wave detection device according to the seventh embodiment of the invention.

FIG. 12 is a block diagram illustrating a schematic configuration of the electromagnetic wave detection device according to the seventh embodiment of the invention. With respect to the electromagnetic wave detection device, in the configuration of the electromagnetic wave detection device shown in FIG. 7, a plurality of mode adjustment means 110 is provided and a multiplex means 140 is provided between the mode adjustment means 110 and the amplification means 120.

With the configuration, electromagnetic waves to be detected are input to the plurality of mode adjustment means 110 so that the spatial mode is adjusted in each of the mode adjustment means 110. Thereafter, the electromagnetic waves output from the plurality of mode adjustment means 110 are input to the multiplex means 140 to be multiplexed. The detected electromagnetic signal waves output from the multiplex means 140 are amplified by the amplification means 120 and also converted to electrical signals by the conversion means 130. The electrical signals output from the conversion means 130 are converted to desired data by the subsequent signal processing system.

According to the embodiment, there is disposed, before the amplification means 120 and the conversion means 130, the plurality of mode adjustment means 110 adjusting the mode of incident multimode electromagnetic waves which are incident in parallel, which makes it possible to collect signal waves with high efficiency even when the electromagnetic waves to be detected are scattered electromagnetic waves or electromagnetic waves with distorted wavefront, thus enabling electromagnetic wave detection at high speed and with high sensitivity, in addition to the effects exerted by the first embodiment. Furthermore, there is provided the multiplex means 140 multiplexing a plurality of electromagnetic waves output from the plurality of mode adjustment means 110, which can further improve the operation stability of the whole device by multiplexing incident electromagnetic waves with the number of modes reduced.

Eighth Embodiment

Figure 13:
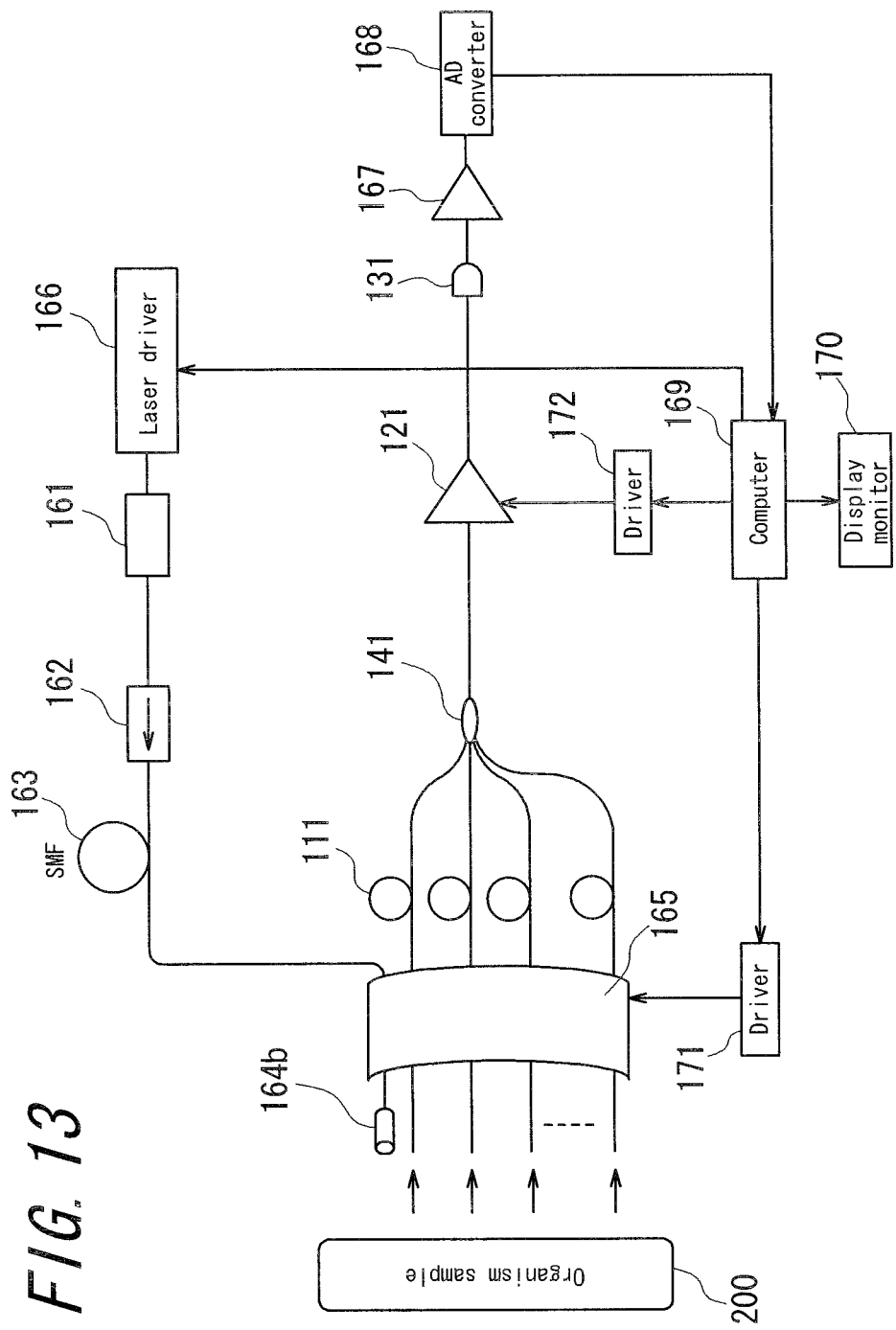
FIG. 13 is a diagram illustrating a schematic configuration of the rigid endoscope blood vessel imaging device according to the eighth embodiment of the invention.

FIG. 13 is a diagram illustrating a schematic configuration of the rigid endoscope blood vessel imaging device according to the eighth embodiment of the invention using the electromagnetic wave detection device shown in FIG. 12. With respect to the rigid endoscope blood vessel imaging device, in the rigid endoscope blood vessel imaging device shown in FIG. 9, a lens for lighting 164b is used instead of a collimator 164a, and a plurality of tapered fibers 111 is provided in parallel and at the output side thereof a fiber coupler 141 is provided as the multiplex means 140. Moreover, the lens for lighting 164b and the plurality of tapered fibers 111 are fixed to the scan mount 165 so that their incidence surfaces are front onto the organism sample 200.

Unlike the collimator 164a shown in FIG. 9, the lens for lighting 164b diffuses laser light having transmitted through the SMF 163 to irradiate the area of organism sample 200 front onto the incidence surface of the tapered fiber 111. The laser light is reflected or scattered in the surface and the inside of the organism sample 200 and incident on the plurality of tapered fibers 111 as multimode light. With respect to the signal light incident on each of tapered fibers 111, its energy distribution among modes is adjusted, thereafter the light is incident, as light with the small number of modes including the fundamental mode, on the fiber coupler 141 to be multiplexed. Then, the signal light multiplexed by the fiber coupler 141 is incident on the Er-doped fluoride optical fiber amplifier 121. Since other configurations and operation are the same as in the sixth embodiment, the same components are represented with the same reference symbols, and the description thereof will be omitted.

According to the embodiment, as explained above, the plurality of tapered fibers 111 is provided, and more light can be collected. Moreover, a device having a smaller number of spatial modes generally achieves more stable operation, so that the operation stability of the whole device can be further improved when multiplexing signal light by the multiplex means with the number of spatial modes reduced.

Ninth Embodiment

Figure 14:
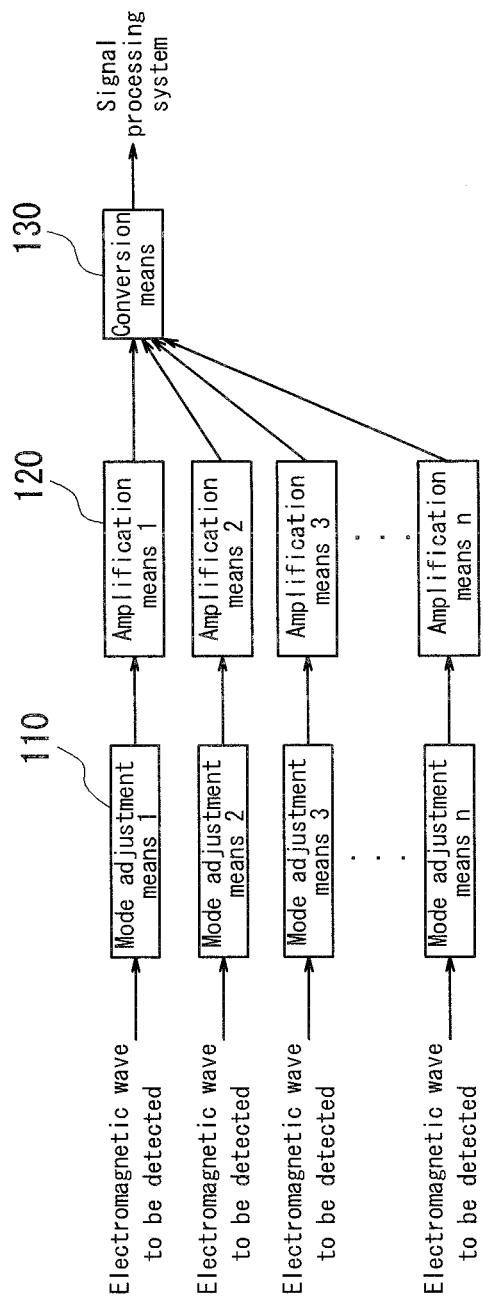
FIG. 14 is a block diagram illustrating a schematic configuration of the electromagnetic wave detection device according to the ninth embodiment of the invention.

FIG. 14 is a block diagram illustrating a schematic configuration of the electromagnetic wave detection device according to the ninth embodiment of the invention. The electromagnetic wave detection device is configured so that one mode adjustment means 110 and one amplification means 120 are paired and a plurality thereof is provided in parallel in the configuration of the electromagnetic wave detection device shown in FIG. 7 and the output from each of the amplification means 120 is input to the conversion means 130 capable of processing the output in parallel.

In the above configuration, electromagnetic waves to be detected are input to the plurality of mode adjustment means 110 so that the spatial mode is adjusted in each of the mode adjustment means 110. Thereafter, electromagnetic waves output from the plurality of mode adjustment means 110 are input to the corresponding amplification means 120 to be amplified, and also converted to electrical signals in parallel by the conversion means 130. The electrical signals output from the conversion means 130 are converted to desired data by the subsequent signal processing system.

According to the embodiment, there are disposed a plurality of mode adjustment means 110 adjusting, by converting the energy mode distribution, incident multimode electromagnetic waves which are incident in parallel to of a mode substantially equal to the amplification spatial mode of the amplification means 120 before the corresponding amplification means 120 and the conversion means 130 respectively, which makes it possible to collect detected electromagnetic waves with high efficiency even when they are scattered electromagnetic waves or electromagnetic waves with distorted wavefront, thus enabling photodetection at high speed and with high sensitivity. Furthermore, a plurality of mode adjustment means 110 and a plurality of amplification means 120 corresponding thereto are provided, and electromagnetic waves output from each of amplification means 120 are converted to electrical signals in parallel, which makes it possible to simultaneously obtain information of a plurality of points such as image information and the like.

Tenth Embodiment

Figure 15:
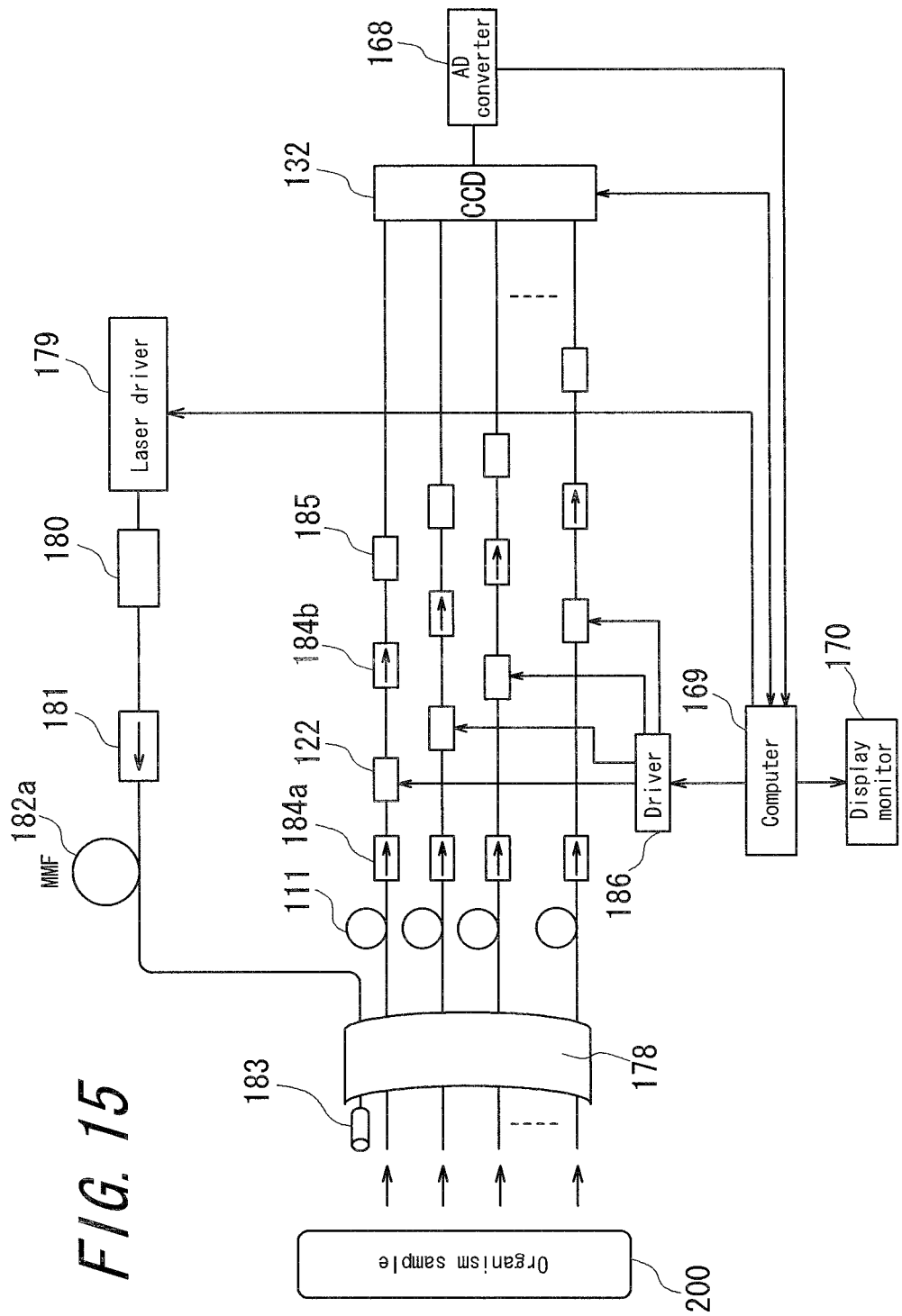
FIG. 15 is a diagram illustrating a schematic configuration of the high sensitivity endoscope according to the tenth embodiment of the invention.

FIG. 15 is a diagram illustrating a schematic configuration of the high sensitivity endoscope according to the tenth embodiment of the invention using the electromagnetic wave detection device shown in FIG. 14. The high sensitivity endoscope is configured so that it irradiates the organism sample 200 with laser light for lighting and the light reflected or scattered in the surface and the inside of the organism sample 200 is detected by the electromagnetic wave detection device shown in FIG. 14 and converted to electrical signals, thereafter the electrical signals are processed by signal processing system to display an image.

As the optical system irradiating the organism sample 200 with laser light for lighting, the high sensitivity endoscope is provided with an LD 180 having a wavelength of 635 nm and output of 20 mW, an isolator 181, a multi-mode fiber (MMF) 182a and a lens for lighting 183, and is configured so that the output from the LD 180 as the light source is output, via the isolator 181 and the MMF 182a, to the air from the lens for lighting 183, with which the organism sample 200 is irradiated.

Moreover, a laser driver 179 driving the LD 180 is provided, and the LD 180 is configured so that its output is controlled through the laser driver 179 by the computer 169 controlling the whole of the high sensitivity endoscope.

Furthermore, The electromagnetic wave detection device detecting light to be detected from the organism sample 200 uses 128×128 tapered fibers 111 as the mode adjustment means 110, 128×128 semiconductor optical amplifiers (SOA) 122 corresponding to each of the tapered fibers 111 as the amplification means 120 and a CCD camera 132 having 128× 128 pixels as the conversion means 130, respectively. Moreover, an isolator 184a is provided between each of tapered fibers 111 and the corresponding SOA 122 respectively, and an isolator 184b and a band-pass filter (BPF) 185 for removing ASE are provided between each of the SOA 122 and the CCD camera 132. The analog-to-digital (AD) converter 168 converting analog electrical signals to digital signals is provided after the CCD camera 132.

It is noted that there is used, as the tapered fiber 111, one having a core diameter at the input side and the output side of 50 μm and 9 μm respectively and a length of 1.0 mm, and it is configured so that the incident surface thereof is front onto the organism sample 200 and signal light from respectively different positions of the organism sample 200 is incident by irradiation with laser light from the lens for lighting 183, and it is fixed, together with the lens for lighting 183, to a housing 178. Moreover, the SOA 122 is configured to be controlled by the computer 169 through the driver 186.

Thus, signal light having a wavelength of 635 nm reflected or scattered in the surface or the inside of the organism sample 200 is input on each of the tapered fibers 111 and its mode is adjusted. Output from each of the tapered fiber 111 is input to the corresponding SOA 122 through the isolator 184 and amplified by about 18 dB. Output from each SOA 122 is incident on the corresponding BPF 185 via the corresponding isolator 184, and ASE is removed. Output from each BPF 185 is input so as to correspond to each pixel of the CCD camera 132 having 128×128 pixels, and converted to electrical signals. Furthermore, signal output converted to electrical signals by the CCD camera 132 is converted to digital signals by the AD converter 168.

Moreover, the high sensitivity endoscope of the embodiment has a computer 169 controlling each unit of the device and processing digital signals output from the AD converter 168. The computer 169 is connected to the laser driver 179 and the driver 186 respectively to control the LD 180 and the SOA 122, and performs signal processing with associating output signals from the AD converter 168 with output of the LD 180 and the gain of the SOA 122 so as to display the result on the display monitor 170 as an endoscope image, for example.

According to the embodiment, as explained above, it is possible to achieve the same effects as in the sixth embodiment and obtain an endoscope image at higher speed and with higher sensitivity as compared with the conventional technique. In the embodiment, moreover, a plurality of tapered fibers 111 and a plurality of SOA 122 corresponding thereto are provided, and it is possible to simultaneously obtain information of a plurality of points of the organism sample 200 by converting optical output from each SOA 122 to electrical signals in parallel. Therefore, the embodiment is effective particularly when generating two-dimensional images.

Furthermore, the SOA 122 is used as the amplification means 122, which makes it possible to constitute a compact and low-cost photodetection system and to integrate with a plurality of semiconductor optical amplifiers or other semiconductor devices such as photodiode (PD) or the like. Moreover, the embodiment also has an advantage that provided power may be small. Furthermore, the SOA can operate in a wider wavelength region as compared with the optical fiber amplifier, and thus it can be applied for a variety of detected light.

Eleventh Embodiment

Figure 16:
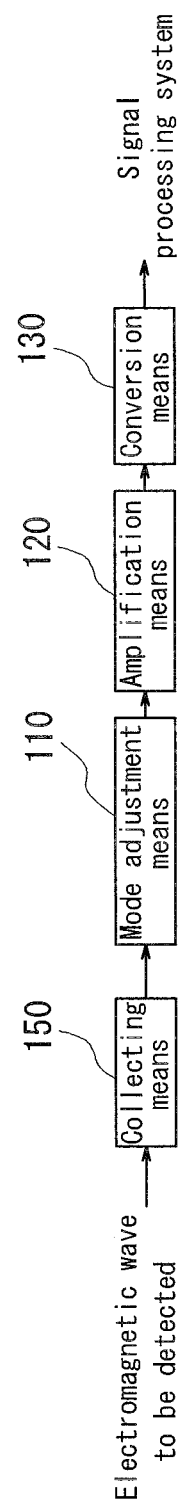
FIG. 16 is a block diagram illustrating a schematic configuration of the electromagnetic wave detection device according to the eleventh embodiment of the invention.

FIG. 16 is a block diagram illustrating a schematic configuration of the electromagnetic wave detection device according to the eleventh embodiment of the invention. With respect to the electromagnetic wave detection device, in the configuration of the electromagnetic wave detection device shown in FIG. 7, a collecting means 150 collecting electromagnetic waves to be detected is provided before the mode adjustment means 110. Thus, it is possible to further increase the amount of signal electromagnetic waves which can be detected, in addition to the effects exerted by the invention of claim 16.

Twelfth Embodiment

Figure 17:
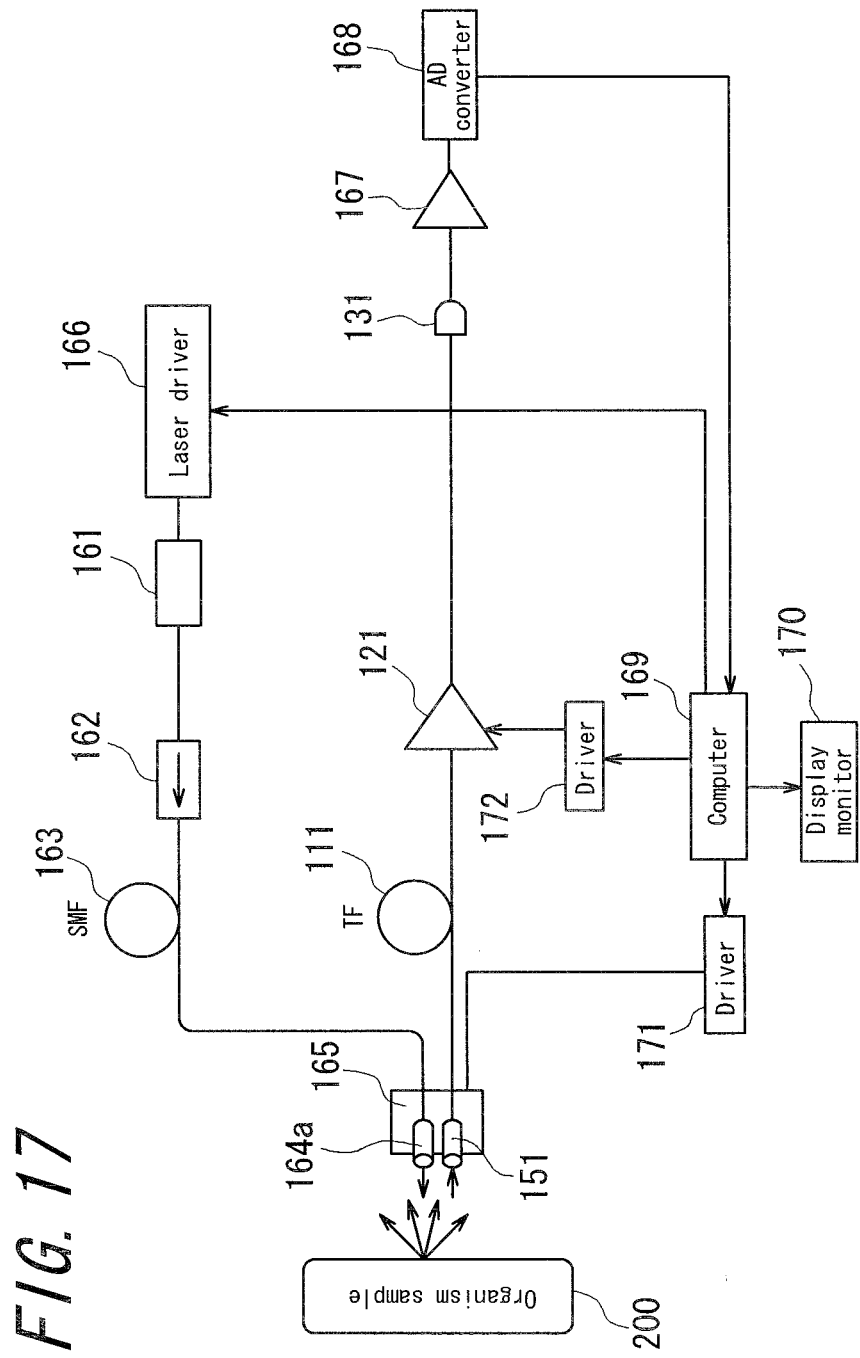
FIG. 17 is a diagram illustrating a schematic configuration of the rigid endoscope blood vessel imaging device according to the twelfth embodiment of the invention.

FIG. 17 is a diagram illustrating a schematic configuration of the rigid endoscope blood vessel imaging device according to the twelfth embodiment of the invention using the electromagnetic wave detection device shown in FIG. 16. With respect to the rigid endoscope blood vessel imaging device, a collective lens 151 is provided before the incidence surface of the tapered fiber 111 in the rigid endoscope blood vessel imaging device shown in FIG. 9. The collective lens 151 is provided before the tapered fiber 111, which makes it possible to take a larger portion of light reflected or scattered in the surface and the inside of the organism sample 200 into the tapered fiber 111. Moreover, there is an advantage that even substances to be detected existent in a deep portion of an object to be detected or far portion therefrom can be also detected with high sensitivity and high SNR.

Thirteenth Embodiment

Figure 18:
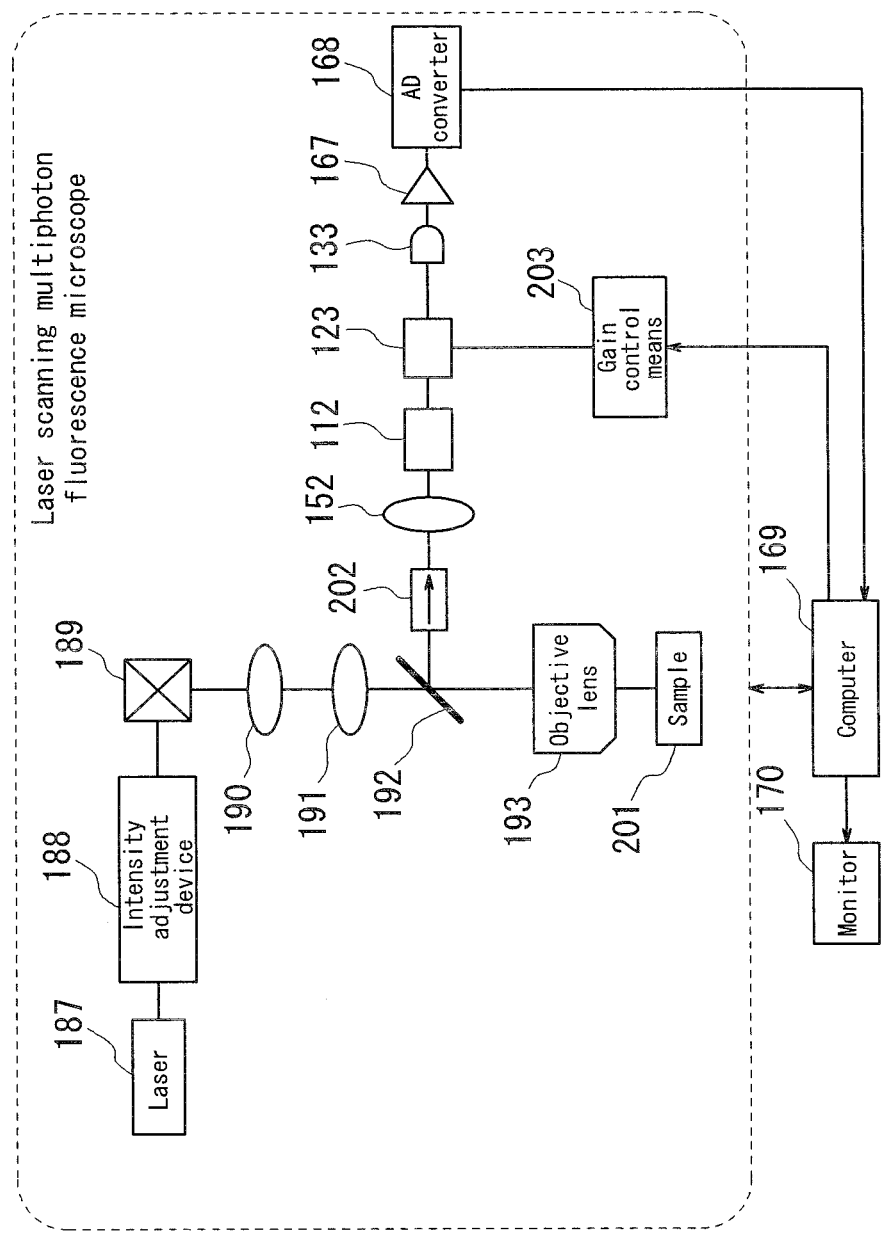
FIG. 18 is a diagram illustrating a schematic configuration of a laser scanning multiphoton fluorescence microscope using the electromagnetic wave detection device according to the thirteenth embodiment of the invention.

FIG. 18 is a diagram illustrating a schematic configuration of a laser scanning multiphoton microscope according to the thirteenth embodiment of the invention. In the embodiment, the electromagnetic wave detection device shown in FIG. 16 is used in the laser scanning multiphoton microscope so as to detect signal light from the living cell sample.

As shown in FIG. 18, the laser scanning multiphoton microscope of the embodiment is constituted including a Titanium-sapphire laser 187, a light intensity adjustment device 188, an X-Y galvano scanner mirror 189, a pupil lens 190, a tube lens 191, a dichroic mirror 192, and an objective lens 193 constituting the objective optical system, an isolator 202, a collective lens 152, a tapered waveguide 112, an SOA 123, a PIN-PD 133, an electric amplifier 167, an AD converter 168 and a gain control means 203.

The Titanium-sapphire laser 187 is a light source generating ultrashort optical pulses having a repetition rate of 80 MHz, a pulse width of 150 fs and an oscillation wavelength of 1060 nm. With respect to the ultrashort optical pulses from the Titanium-sapphire laser 187, their optical average power is adjusted to 100 mW by the light intensity adjustment device 188, and the pulses pass through the X-Y galvano scanner mirror 189, the pupil lens 190, the tube lens 191, the dichroic mirror 192 and the objective lens 193 and are collected so that the living cell sample 201 to be inspected is irradiated therewith. At that time, the X-Y galvano scanner mirror 189 is driven to scan the position on the sample irradiated with laser light. Thus, it is possible to generate fluorescence in a desired area in the living cell sample 201 through multiphoton excitation (two-photon excitation, for example) of red fluorescent protein (DsRed), for example.

Moreover, the objective lens 193 guides fluorescence generated from the living cell sample 201 to the dichroic mirror 192. The dichroic mirror 192 is configured so as to allow light having a wavelength of 1060 nm from the Titanium-sapphire laser 187 to pass therethrough and so as to reflect light having a short wavelength of 700 nm or shorter. Thus, fluorescence having a wavelength of about 570 nm to 650 nm generated in the living cell sample 201 is reflected by the dichroic mirror 192.

The collective lens 152, the tapered waveguide 112, the SOA 123 and the PIN-PD 133 correspond respectively to the collecting means 150, the mode adjustment means 110, the amplification means 120 and the conversion means 130 of the electromagnetic wave detection device shown in FIG. 16. The fluorescence reflected by the dichroic mirror 192 is collected by the collective lens 152 via the isolator 202 and input to the tapered waveguide 112. The tapered waveguide 112 has 8 spatial modes at the incidence side, and is configured so that the number of modes is decreased to 2 at the output side by mode adjustment. The fluorescence output from the tapered waveguide 112 is incident on the SOA 123 controlled by the external computer 169 through the gain control means 203 and amplified, thereafter the silicon PIN-PD 133 converts it to electrical signals. Since the number of modes of incident signal light is decreased, the SOA 123 can suppress the occurrence of ASE and perform amplification with high SNR.

Furthermore, electrical signals output from the PIN-PD 133 are amplified by the electric amplifier 167, converted to digital signals by the AD converter 168 and transmitted to the external computer 169. The computer 169 performs signal processing with associating signals received from the AD converter 168 with information of scanned positions and the like obtained from the X-Y galvano scanner mirror 189 and displays the result on the monitor 170 as a microscope image.

It is noted that, in the laser scanning multiphoton fluorescence microscope, the fluorescence generated from the living cell sample 201 through two-photon excitation, for example, by excitation optical pulses from the Titanium-sapphire laser 187 lasts for about some nanoseconds. That is, the fluorescence generated from the living cell sample 201 becomes pulse light synchronized with excitation optical pulses from the Titanium-sapphire laser 187. Thus, in the embodiment, the computer 169 controls so that, in synchronization with the timing at which the pulse form of fluorescence is incident on the SOA 123, the gain of the SOA 123 is increased at the timing of incidence of fluorescence.

According to the embodiment, fluorescence generated from the living cell sample 201 through multiphoton excitation by excitation optical pulses from the Titanium-sapphire laser 187 is subjected to mode adjustment so that the number of spatial modes is decreased using the tapered waveguide 112, amplified by the SOA, and then photoelectrically converted by the silicon PIN-PD 133. Thus, it is possible to photoelectrically convert fluorescence resulted by two-photon excitation with high sensitivity and at high speed without excessively increasing the intensity of laser light with which the living cell sample 201 is irradiated even when fluorescence as signal light obtained from the living cell sample 201 is weak.

In addition, the gain of the SOA 123 is controlled in synchronization with the timing of incidence of fluorescence on the SOA 123, which can reduce the mixture of ASE generated by providing power to the optical amplifier during time in which fluorescence is not incident, thus improving the S/N. Furthermore, it is possible to easily adjust the level of signals to be detected by varying the gain of the SOA 123.

Fourteenth Embodiment

Figure 19:
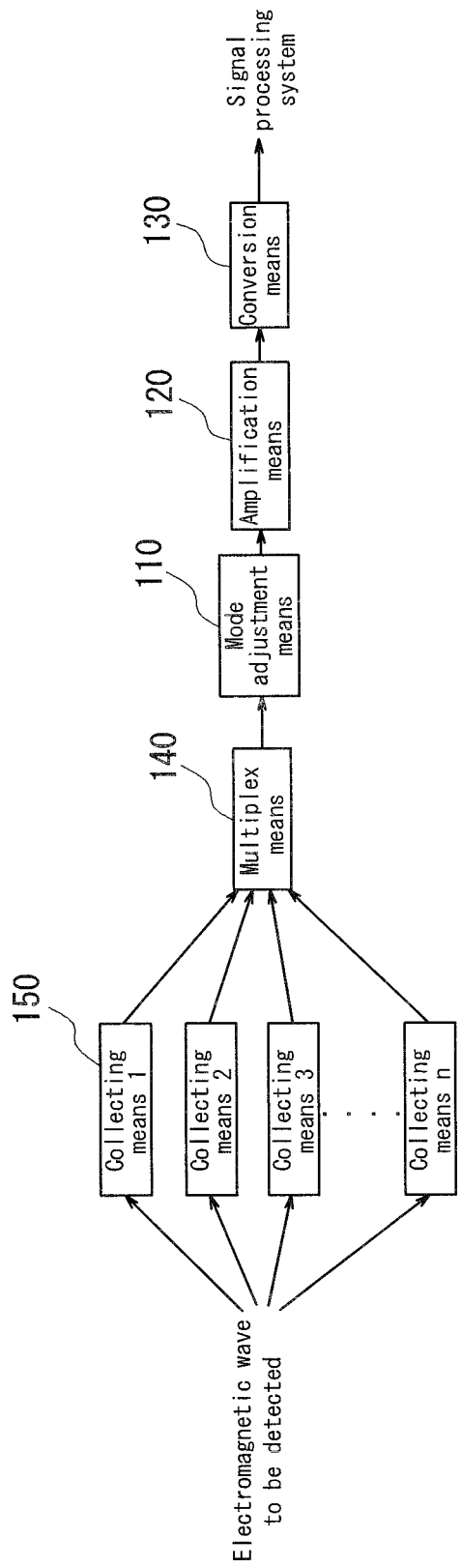
FIG. 19 is a block diagram illustrating a schematic configuration of the electromagnetic wave detection device according to the fourteenth embodiment of the invention.

FIG. 19 is a block diagram illustrating a schematic configuration of the electromagnetic wave detection device according to the fourteenth embodiment of the invention. With respect to the electromagnetic wave detection device, in the configuration of the electromagnetic wave detection device shown in FIG. 7, a plurality of collecting means 150 and the multiplex means 140 multiplexing detected electromagnetic waves from the plurality of collecting means 150 are provided before the mode adjustment means 110.

In the above configuration, electromagnetic waves to be detected are collected by the plurality of collecting means 150 and input to the multiplex means 140. The multiplex means 140 multiplexes the input plurality of detected light, and outputs it to the mode adjustment means 110. The other operation is the same as in the electromagnetic wave detection device in FIG. 7.

According to the embodiment, a plurality of collecting means 150 is provided, which makes it possible to collectively obtain signal electromagnetic waves from a plurality of parts and, further, multiple means 140 collects the signal electromagnetic waves from a plurality of parts, which increases the energy of the signal electromagnetic waves input to the amplification means 120 and further improves the SNR.

Fifteenth Embodiment

Figure 20:
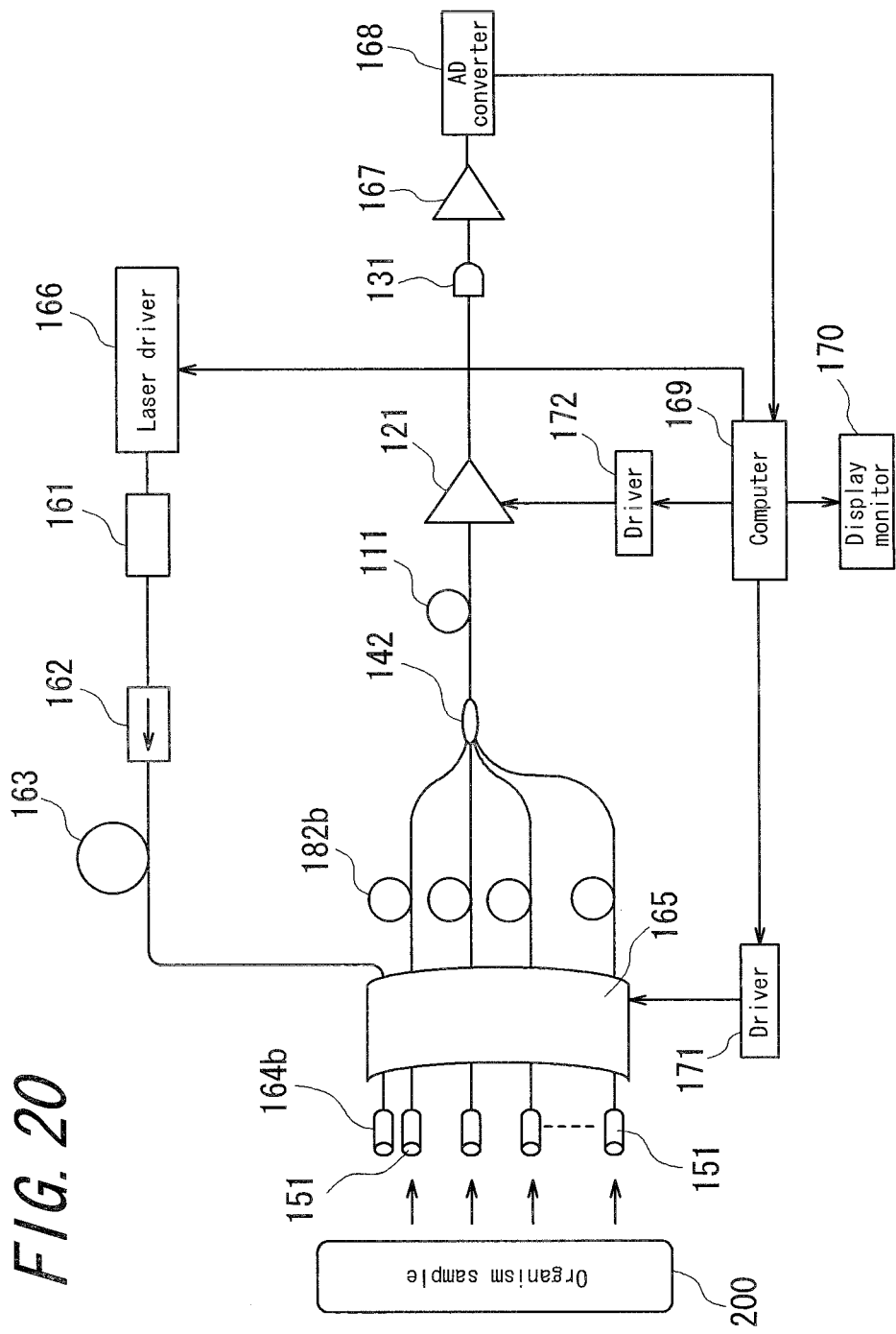
FIG. 20 is a diagram illustrating a schematic configuration of the rigid endoscope blood vessel imaging device according to the fifteenth embodiment of the invention.

FIG. 20 is a diagram illustrating a schematic configuration of rigid endoscope blood vessel imaging device according to the fifteenth embodiment of the invention shown in FIG. 19. With respect to the rigid endoscope blood vessel imaging device, in the rigid endoscope blood vessel imaging device shown in FIG. 9, the lens for lighting 164b is used instead of the collimator 164a and there are provided, before the tapered fiber 111, a plurality of collective lenses 151, a plurality of multi-mode fiber (MMF) 182b connected to the collective lenses 151 and the multimode fiber coupler 142 multiplexing signal light from each MMF 182b. It is noted that the collective lens 151 and the multimode fiber coupler 142 correspond respectively to the collecting means 150 and the multiplex means 140 in FIG. 19.

Moreover, the lens for lighting 164b and each collective lens 151 are fixed to the scan mount 165 so that they are front onto the sample 200. Furthermore, unlike the collimator 164a shown in FIG. 9, the lens for lighting 164b diffuses laser light having transmitted through the SMF 163 to irradiate the area of the organism sample 200 front onto the incidence surface of each collective lens 151.

Thus, laser light emitted from the lens for lighting 164b is reflected or scattered in the surface and the inside of the organism sample 200, collected by the plurality of collective lens 151 and multiplexed by the multimode fiber coupler 142 through the MMF 182b, thereafter it is incident on the tapered fiber 11 as multimode light. Since other configurations and operation are the same as in the sixth embodiment, the same components are represented with the same reference symbols, and the description thereof will be omitted.

According to the embodiment, as explained above, the plurality of collective lenses 151 is provided, which make it possible to collectively obtain signal light from a plurality of parts and thus to further increase the amount of signal light which can be detected. Moreover, signal light from a plurality of parts is collected by the multimode fiber coupler 142 and thus the number of the subsequent tapered fiber 111, Er-doped fluoride optical fiber amplifier 121 and PIN-PD 131 can be reduced to one. In addition, signal light from a plurality of parts is collected, which can increase signal light energy input to the Er-doped fluoride optical fiber amplifier 121. Therefore, it becomes possible to obtain an endoscope image at higher speed and with higher sensitivity.

Sixteenth Embodiment

Figure 21:
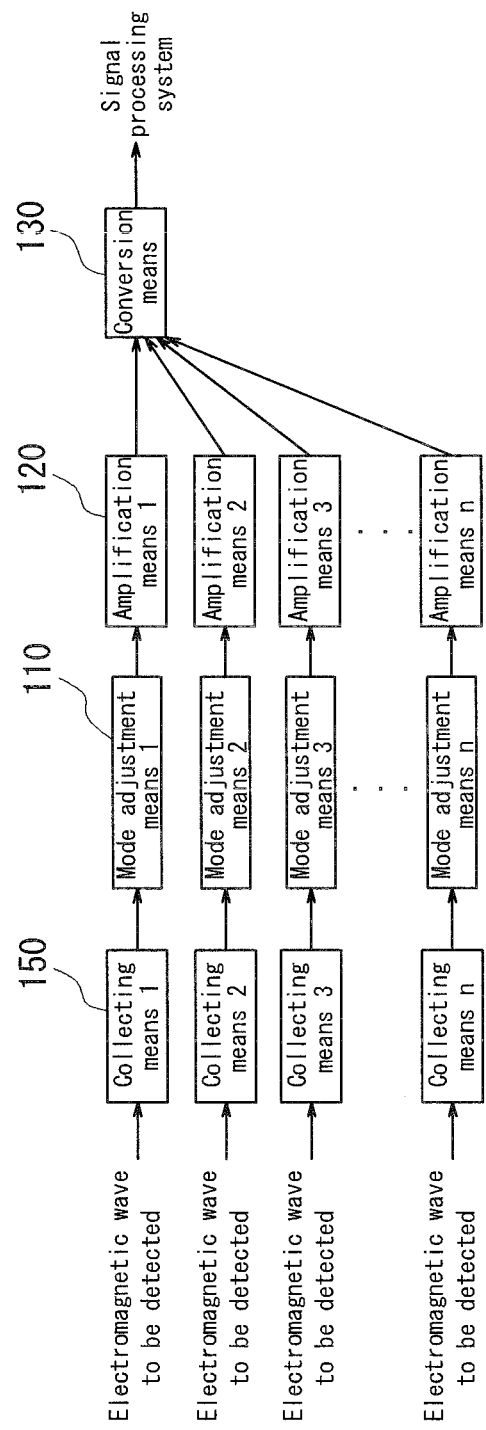
FIG. 21 is a block diagram illustrating a schematic configuration of the electromagnetic wave detection device according to the sixteenth embodiment of the invention.

FIG. 21 is a block diagram illustrating a schematic configuration of the electromagnetic wave detection device according to the sixteenth embodiment of the invention. With respect to the electromagnetic wave detection device, the collecting means 150 is provided before each mode adjustment means 110 in the configuration of the electromagnetic wave detection device shown in FIG. 14. Thus, it becomes possible to guide a larger amount of detected electromagnetic wave to the mode adjustment means 110, in addition to the effects exerted by the electromagnetic wave detection device according to the ninth embodiment.

Seventeenth Embodiment

Figure 22:
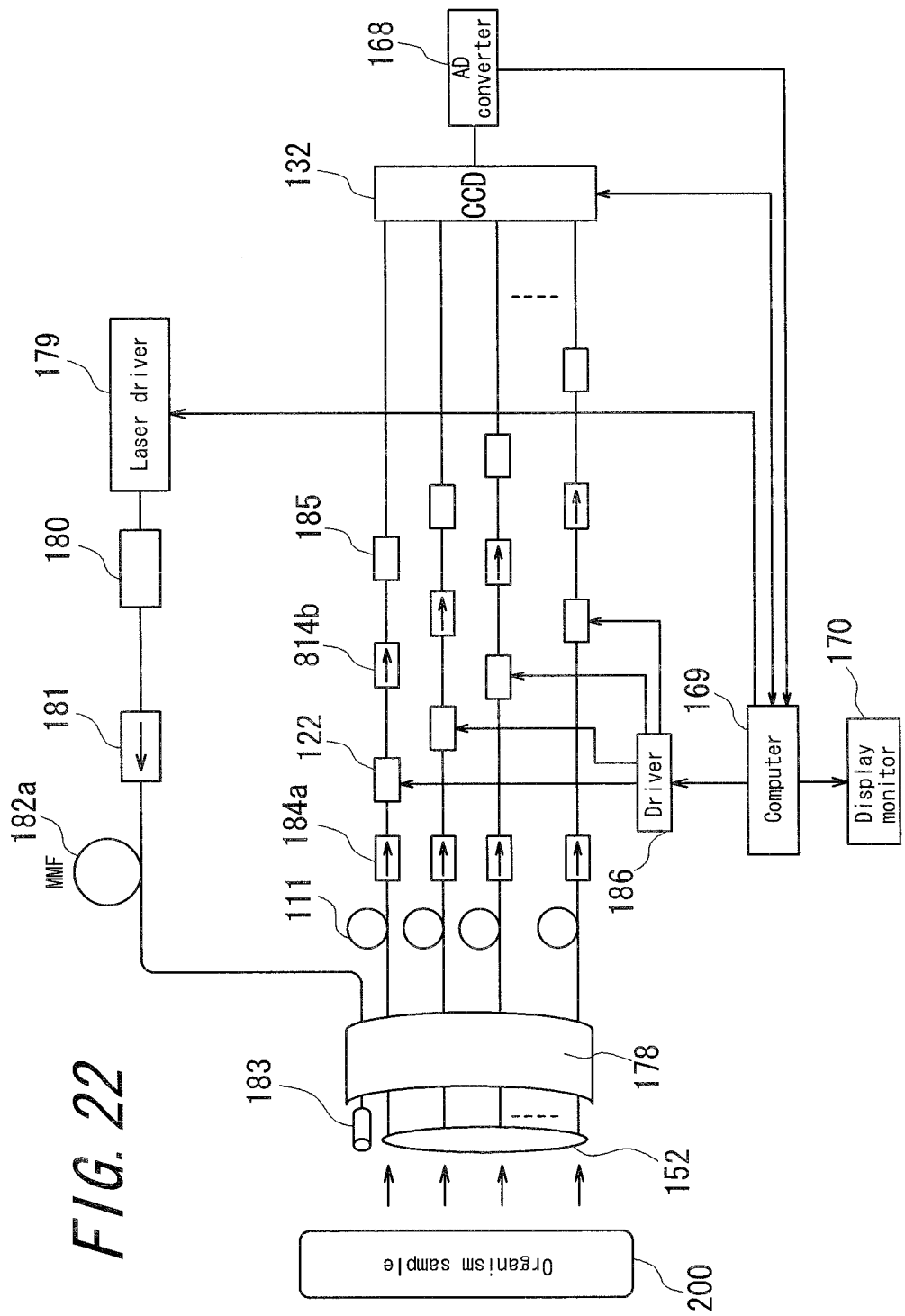
FIG. 22 is a diagram illustrating a schematic configuration of the rigid endoscope blood vessel imaging device according to the seventeenth embodiment of the invention.

FIG. 22 is a diagram illustrating a schematic configuration of the rigid endoscope blood vessel imaging device according to the seventeenth embodiment of the invention using the electromagnetic wave detection device shown in FIG. 21. With respect to the rigid endoscope blood vessel imaging device, the collective lens 152 is provided before the plurality of tapered fibers 111 in the rigid endoscope blood vessel imaging device according to the tenth embodiment shown in FIG. 15. The collective lens 152 is provided before the tapered fiber 111, which makes it possible to take a larger portion of light reflected or scattered in the surface and the inside of the organism sample 200 into each tapered fiber 111. Since other configurations and operation are the same as in the tenth embodiment, the same components are represented with the same reference symbols, and the description thereof will be omitted.

According to the embodiment, as explained above, the collective lens 152 is provided before the tapered fiber 111, which make it possible to further increase the amount of signal light which can be detected. Therefore, it becomes possible to obtain an endoscope image at higher speed and with higher sensitivity.

It is noted that the invention is not limited to the above embodiments, and many variations and modifications can be implemented. For example, the laser scanning confocal fluorescence microscope 51 shown in the second embodiment and the laser scanning multiphoton fluorescence microscope 71 shown in the third embodiment are not limited to of reflection type, and can be configured as of transmission type. Similarly, the laser scanning CARS microscope 81 shown in the fourth embodiment is not limited to of transmission type and can be configured as of reflection type, respectively.

Moreover, although the tapered fiber 111 or the tapered waveguide 112 is used as the mode adjustment means, the means is not limited thereto, and a tapered photonic crystal waveguide, a long-period fiber bragg grating, a refractive-index modulation flat waveguide or the like can be used.

For example, in the thirteenth embodiment, there can be used, instead of the tapered waveguide 112, a refractive-index distribution type waveguide having nonuniform refractive-index distribution in a longitudinal direction of the waveguide or a waveguide having nonuniform stress distribution or nonuniform temperature distribution in a longitudinal direction of the waveguide. In this case, the variation of refractive-index, stress or temperature in the optical waveguide causes energy transfer among spatial modes. Such variation of refractive-index, stress or temperature is intentionally given into the optical waveguide, which can induce the variation of energy ratio among spatial modes.

Moreover, although the Er-doped fluoride optical fiber amplifier or the SOA is used as the amplification means 120 in the fifth to seventeenth embodiments, the means is not limited thereto. For example, instead of these amplifiers, there can be used an optical fiber amplifier using stimulated Raman scattering effects. The wavelength region where the rare-earth-doped optical fiber amplifier operates is very discrete, and thus there is wavelength region in which optical amplifying effects cannot be obtained. However, since the optical fiber amplifier using stimulated Raman scattering effects do not specify the wavelength region where it operates, the use thereof enables optical amplification in any wavelength region. Moreover, other optical fiber amplifiers like a fiber Brillouin optical amplifier, a fiber parametric optical amplifier and the like can be also used. Furthermore, a dye amplifier can be also used. Since the dye has a wider range of amplification band as compared with the fiber amplifier or the semiconductor optical amplifier, the use thereof enables amplification of a wider band range of signals. In addition, the optical amplification at a variety of wavelengths becomes possible, depending on design of the dye.

Moreover, although the PIN-PD or the CCD camera is used as the conversion means 130, the means is not limited thereto, and APD, PMT, CMOS, EM-CCD or EB-CCD can be used, for example.

Although the fiber coupler or the multimode fiber coupler is used as the multiplex means 140, the means is not limited thereto, and a flat waveguide optical coupler, a spatial beam combiner, a polarized wave synthesis coupler, a wavelength synthesis coupler and the like, for example, can be also used.

Although the collective lens is used as the collecting means, the means is not limited thereto, and a Gradient Index (GRIN) lens, a lensed fiber or the like can be used, for example.

Moreover, the invention can be effectively applied not only to the imaging device, the endoscope and the like shown in the above embodiments but also to the case in which the above optical measurement method such as flow site meter, FCS, SPR, LPIA, FIA or the like is performed.

It is noted that, as explained in the above fifth to seventeenth embodiments, the inventions according to the sixteenth to the thirty-eighth aspects of the application have the following effects.

Moreover, according to the invention of the sixteenth aspect of the application, there is disposed the mode adjustment means adjusting, by converting the energy mode distribution, incident multimode electromagnetic waves to of a mode substantially equal to the amplification spatial mode of the amplification means before the amplification means and the conversion means, which makes it possible to collect electromagnetic waves to be detected with high efficiency even when they are scattered electromagnetic waves or electromagnetic waves with distorted wavefront, thus enabling electromagnetic wave detection at high speed and with high sensitivity.

Furthermore, according to the invention of the seventeenth aspect of the application, the mode adjust means reduces the number of spatial modes of incident electromagnetic waves, which makes it possible to reduce the number of spatial modes with small loss, thus enabling electromagnetic amplification with high SNR by the amplification means, in addition to the effects exerted by the invention in claim 16.

Moreover, according to the invention of the eighteenth aspect of the application, the energy ratio among spatial modes of incident electromagnetic waves is varied, which can vary the energy ratio among spatial modes, in addition to the effects exerted by the invention in claim 16. Thus, a large amount of energy is concentrated to a part of spatial modes, and the artificial reduction of the number of spatial modes can be achieved.

Furthermore, according to the invention of the nineteenth aspect of the application, the waveguide is used as the mode adjust means, which can achieve variation of spatial modes with high stability, in addition to the effects exerted by the invention in claim 16.

Moreover, according to the invention of the twentieth aspect of the application, the optical fiber is used as the waveguide, which can stably achieve a long spatial-mode-adjustment waveguide, in addition to the effects exerted by the invention in claim 19. When the waveguide is longer, it becomes possible to adjust the spatial mode adiabatically, thus enabling the spatial mode adjustment with smaller loss. Moreover, the use of optical fiber makes fine adjustment of the spatial optical system unnecessary, thus improving the degree of freedom in use.

Furthermore, according to the invention of the twenty-first aspect of the application, there is used, as the mode adjustment means, the tapered optical fiber with a degree of freedom in design being significantly high among optical fibers, which achieves the mode adjustment means suitable for the condition of light to be detected, in addition to the effects exerted by the invention in claim 20. Moreover, the tapered fiber can be produced relatively easily, which makes it possible to provide a low-cost photodetection device.

Moreover, according to the invention of the twenty-second aspect of the application, the variation of refractive-index, stress or temperature is intentionally given into the optical waveguide, which can induce the variation of energy ratio among spatial modes, in addition to the effects exerted by the invention in claim 19.

Furthermore, according to the invention of the twenty-third aspect of the application, the optical fiber amplifier is used as the amplification means, which enables optical amplification with high gain and low noise, in addition to the effects exerted by the invention in claim 16.

Moreover, according to the invention of the twenty-fourth aspect of the application, the rare-earth-doped optical fiber amplifier is used as the optical fiber amplifier, which enables optical amplification with high gain, low noise and high efficiency, in addition to the effects exerted by the invention in claim 23.

Furthermore, according to the invention of the twenty-fifth aspect of the application, the rare-earth-doped fluoride optical fiber amplifier is used as the rare-earth-doped optical fiber amplifier, which enables optical amplification in wavelength regions where no operation is possible with the Silica optical fiber amplifier, in addition to the effects exerted by the invention in claim 24. Particularly, the efficient optical amplification in visible bands becomes possible.

Moreover, according to the invention of the twenty-sixth aspect of the application, there is used, as the fiber amplifier, the optical fiber amplifier using stimulated Raman effects, which enables optical amplification in any wavelength regions, in addition to the effects exerted by the invention in claim 23.

Furthermore, according to the invention of the twenty-seventh aspect of the application, the semiconductor optical amplifier is used as the amplification means, which makes it possible to constitute a compact and low-cost photodetection system, in addition to the effects exerted by the invention in claim 16.

Moreover, according to the invention of the twenty-eighth aspect of the application, the optical amplifier including dye is used as the amplification means, which makes it possible to amplify a wider band range of signals, in addition to the effects exerted by the invention in claim 16. Furthermore, the optical amplification at a variety of wavelengths becomes possible, depending on design of the dye.

Furthermore, according to the invention of the twenty-ninth aspect of the application, the amplification means varies the gain depending on the timing of incidence of incident electromagnetic waves, which can prevent, in detecting intermittent signal light, mixture of excessive noises by turning the optical amplifier on or off in synchronization with the signal light, in addition to the effects exerted by the invention in claim 16.

Moreover, according to the invention of the thirtieth aspect of the application, the collecting means is used before the mode adjust means, which can further increase the amount of incident electromagnetic waves which can be detected, in addition to the effects exerted by the invention in claim 16.

Furthermore, according to the invention of the thirty-first aspect of the application, a plurality of collecting means is provided, which makes it possible to collectively obtain incident electromagnetic waves from a plurality of parts and thus further increase the amount of incident electromagnetic waves which can be detected, in addition to the effects exerted by the invention in claim 16.

Moreover, according to the invention of the thirty-second aspect of the application, the multiplex means collects incident electromagnetic waves from a plurality of parts, which can reduce the number of the subsequent mode adjustment means, amplification means and conversion means, in addition to the effects exerted by the invention in claim 31. Besides, incident electromagnetic waves from a plurality of parts are collected, which can increase the energy of incident electromagnetic waves input to the amplification means.

Furthermore, according to the invention of the thirty-third aspect of the application, there is disposed a plurality of mode adjustment means adjusting, by converting the energy mode distribution, incident multimode electromagnetic waves which are incident in parallel to of a mode substantially equal to the amplification spatial mode of the amplification means before the amplification means and the conversion means, which makes it possible to collect signal waves with high efficiency even when incident electromagnetic waves are scattered electromagnetic waves or electromagnetic waves with distorted wavefront, thus enabling photodetection at high speed and with high sensitivity. In addition, there is provided the multiplex means multiplexing a plurality of electromagnetic waves output from a plurality of mode adjustment means, which can further improve the operation stability of the whole device when multiplexing electromagnetic waves with the number of modes reduced.

Moreover, according to the invention of the thirty-fourth aspect of the application, there is disposed a plurality of mode adjustment means adjusting, by converting the energy mode distribution, incident multimode electromagnetic waves which are incident in parallel to of a mode substantially equal to the amplification spatial mode of the amplification means before each corresponding amplification means and conversion means, which makes it possible to collect signal waves with high efficiency even when incident electromagnetic waves are scattered electromagnetic waves or electromagnetic waves with distorted wavefront, thus enabling photodetection at high speed and with high sensitivity. In addition, a plurality of mode adjustment means and a plurality of amplification means corresponding thereto are provided, and electromagnetic waves output from each of amplification means are converted to electrical signals in parallel, which makes it possible to simultaneously obtain information of a plurality of points such as image information and the like.

Furthermore, according to the invention of the thirty-fifth aspect of the application, incident multimode electromagnetic waves are adjusted to of a mode substantially equal to the amplification spatial mode at the amplification step by converting the energy mode distribution, which makes it possible to collect the incident electromagnetic waves with high efficiency even when they are scattered electromagnetic waves or electromagnetic waves with distorted wavefront, thus enabling photodetection at high speed and with high sensitivity.

Moreover, according to the invention of the thirty-sixth aspect of the application, electromagnetic waves to be detected obtained from an organism are detected by the electromagnetic wave detection device described in any one of claims 16 to 35, which makes it possible to collect electromagnetic waves to be detected with high efficiency even when they are scattered electromagnetic waves or electromagnetic waves with distorted wavefront, thus enabling observation of the organism through electromagnetic wave detection at high speed and with high sensitivity.

Furthermore, according to the invention of the thirty-seventh aspect of the application, there is provided the electromagnetic wave detection device described in any one of claims 16 to 35, which makes it possible to collect electromagnetic waves to be detected with high efficiency even when they are scattered electromagnetic waves or electromagnetic waves with distorted wavefront, thus enabling microscope observation through electromagnetic wave detection at high speed and with high sensitivity.

Moreover, according to the invention of the thirty-eighth aspect of the application, there is used the electromagnetic wave detection device described in any one of claims 16 to 35, which makes it possible to collect electromagnetic waves to be detected with high efficiency even when they are scattered electromagnetic waves or electromagnetic waves with distorted wavefront, thus enabling generation of endoscope image through electromagnetic wave detection at high speed and with high sensitivity.

There will be described an example in which the optical detection device according to the first aspect of the application is applied in the optical tomographic image generation device. Before explaining the optical tomographic image generation device according to the invention of the application, there will be described a reference example of the optical tomographic image generation device which has been developed together with the invention of the application.

First Reference Example

Figure 23:
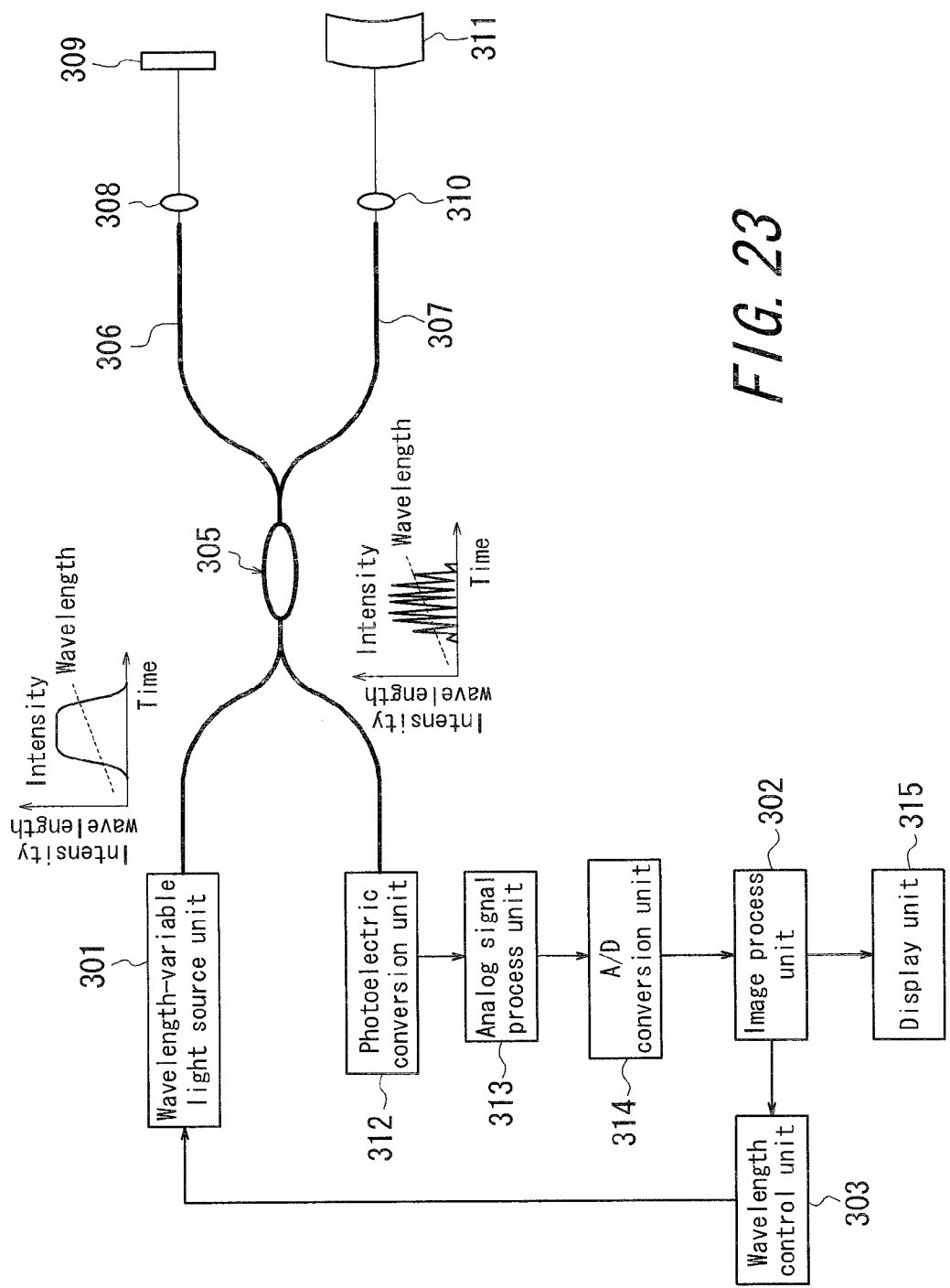
FIG. 23 is a functional block diagram illustrating a fundamental configuration of the optical tomographic image generation device according to the first reference example of the invention.

FIG. 23 is a functional block diagram illustrating a fundamental configuration of the optical tomographic image generation device according to the first reference example of the application. The optical tomographic image generation device has a wavelength-variable light source unit 301 which can control the wavelength of light to be emitted. The wavelength-variable light source unit 301 is controlled by an image process unit 302 having a personal computer through a wavelength control unit 303, so that the wavelength-variable light source unit 301 emits light having a smooth variation of light intensity and a wavelength varying with time, as shown in FIG. 23.

The wavelength-variable light source unit 301 is connected to one end of an optical multiplex-demultiplex unit 305. The optical multiplex-demultiplex unit 305 demultiplexes light from the wavelength-variable light source unit 301 to two, and causes one to be incident, as reference light, on a reference-side optical transmission unit 306 and the other to be incident, as inspection light, on a inspection-side optical transmission unit 307. The reference light incident on the reference-side optical transmission unit 306 is emitted from the reference-side optical transmission unit 306, passes through a lens 308 and is reflected by a light reflection unit 309, thereafter the reflected reference light passes through the lens 308 again, is transmitted through the reference-side optical transmission unit 306 and incident on the optical multiplex-demultiplex unit 305.

On the other hand, the inspection light demultiplexed by the optical multiplex-demultiplex unit 305 and incident on the inspection-side optical transmission unit 307 is emitted from the inspection-side optical transmission unit 307 and passes through a lens 310, thereafter an object to be inspected 311 such as an organism or the like is irradiated with the light. The inspection light with which the object to be inspected 311 has been irradiated is reflected and scattered in the surface and the inside of the object. With respect to the reflected and scattered inspection light, one part thereof is rendered to pass through the lens 310 and is incident on the inspection-side optical transmission unit 307 again, thereafter it is transmitted through the inspection-side optical transmission unit 307 and incident on the optical multiplex-demultiplex unit 305 again.

The optical multiplex-demultiplex unit 305 multiplexes reflected reference light and reflected inspection light incident respectively from the reference-side optical transmission unit 306 and the inspection-side optical transmission unit 307 to generate interference light such as one shown in FIG. 23. The interference light generated by the optical multiplex-demultiplex unit 305 is received by a photoelectric conversion unit 312 and photoelectrically converted.

The photoelectric conversion signals output from the photoelectric conversion unit 312 are provided to an analog signal process unit 313, and the analog signal process unit 313 attenuates low-frequency components of the photoelectric conversion signals relative to high-frequency components thereof. That is, in the analog signal process unit 313, a High-Pass Filter (HPF) or a Band-Pass Filter (BPF) removes low-frequency components of the photoelectric conversion signals, and a high-frequency amplifier amplifies only high-frequency components or high-frequency components are amplified while reducing low-frequency components, for example. The analog output signals from the analog signal process unit 313 are converted to digital signals by an analog-digital (A/D) conversion unit 314 and provided to the image process unit 302.

The image process unit 302 performs Fourier transformation for digital output signals from the A/D conversion unit 314 and converts the frequency to spatial distance. Therefore, the information corresponds to optical signals reflected and scattered in each depth position at which the inspection-side optical transmission unit 307 irradiates the object to be inspected 311 with inspection light. The image process unit 302 obtains information from each depth position, as described above, every time a position of the object to be inspected 311 which the inspection-side optical transmission unit 307 irradiates with inspection light is varied, and generates a tomographic image of the object to be inspected 311 based on such information to display it on a display unit 315.

As above, before the A/D conversion unit 314 converts photoelectric conversion signals of interference light of reflected reference light and reflected inspection light obtained from the photoelectric conversion device 312 to digital signals, the analog signal process unit 313 attenuates low-frequency components relative to high-frequency components, which can emphasize information from deep portion of the object to be inspected 311. Therefore, when analog output signals from the analog signal process unit 313 are converted to digital signals by the A/D conversion unit 314 later, it is possible to convert information from the deep portion of the object to be inspected 311 to digital signals with high accuracy without burying the information in quantization noises, thus improving the penetration depth of a tomographic image.

Next, a concrete embodiment of the first reference example will be described with reference to the accompanying drawings.

Figure 24:
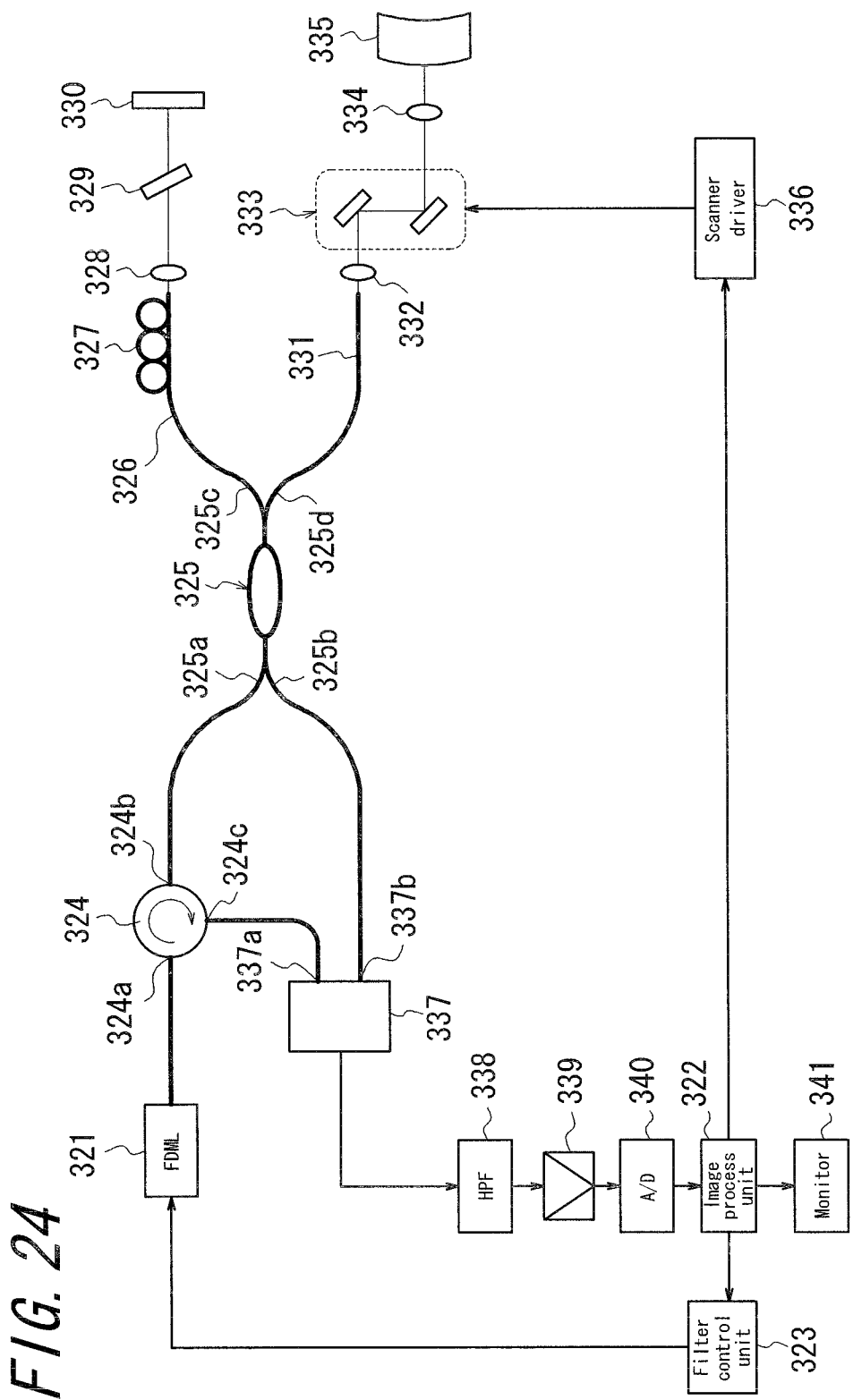
FIG. 24 is a functional block diagram illustrating a configuration of the optical tomographic image generation device according to the first reference example of the invention

FIG. 24 is a functional block diagram illustrating a configuration of the optical tomographic image generation device according to the first reference example of the invention. In the embodiment, a Fourier domain mode locked laser (FDML) 321 is used as the wavelength-variable light source unit. The FDML 321 is constituted by a semiconductor optical amplifier (SOA), a fiber Fabry-Perot wavelength tunable filter (FFPTF), an optical isolator, a single-mode fiber (SMF) and an optical fiber coupler for output, as disclosed in US 2006/0,187,537, for example. A plurality kinds of SMF is used and the total length thereof is 4.3 km, and wavelength distribution of the whole of a laser resonator is arranged to be nearly zero.

In the embodiment, an image process unit 322 having a personal computer controls FFPTF of an FDML 321 through a filter control unit 323 so as to output, from the FDML 321, light having a swept wavelength range of 1010 nm to 1090 nm, a repetition rate of 50 kHz and optical average power of about 5 mW.

The output end of the FDML 321 is connected to a first port 24a of an optical circulator 324 having the first port 24a to the third port 24c. The optical circulator 324 outputs light input from the first port 24a to the second port 24b, and outputs light input from the second port 24b from the third port 24c.

The second port 324b of the optical circulator 324 is connected to a first port 325a of a 3 dB coupler 325 as the optical multiplex-demultiplex unit having a first port 325a to the fourth port 325d, and the 3 dB coupler 325 demultiplexes light input to the first port 325a to the third port 325c and the fourth port 325d with an intensity ratio of 50:50 respectively.

The third port 325c of the 3 dB coupler 325 is connected to a single-mode fiber (SMF) 326 as the reference-side optical transmission unit, and light demultiplexed by the 3 dB coupler 325 is input to the SMF 326 as reference light. The SMF 326 is provided with a polarization controller 327 along the path thereof to adjust a polarization state of reference light. The reference light having transmitted through the SMF 326 is converted to a parallel beam by a lens 328 and emitted into the air, thereafter the emitted reference light is attenuated by an optical attenuator 329 to have a desired light intensity and then reflected by a reflective mirror 330. The reference light reflected by the reflective mirror 330 is rendered to be incident on the SMF 326 through the optical attenuator 329 and the lens 328, and input to the third port 325c of the 3 dB coupler 325.

On the other hand, the fourth port 325d of the 3 dB coupler 325 is connected to an SMF 331 as the inspection-side optical transmission unit, and light demultiplexed by the 3 dB coupler 325 is input to the SMF 331 as inspection light. The inspection light having transmitted through the SMF 331 is converted to a parallel beam by a lens 332 and emitted into the air, thereafter transmitted direction of the emitted inspection light is two-dimensionally scanned by a galvano scanner mirror 333 and collected by the lens 334 on the object to be inspected 335 such as an organism and the like. The galvano scanner mirror 333 is controlled by the image process unit 322 through a scanner driver 336. The inspection light reflected and scattered in the surface or the inside of the object to be inspected 335 is rendered to be transmitted, as reflected inspection light, through the lens 334, the galvano scanner mirror 333, the lens 332 and the SMF 331 again and input to the fourth port 325d of the 3 dB coupler 325.

The reflected reference light input to the third port 325c of the 3 dB coupler 325 and the reflected inspection light input to the fourth port 325d thereof are rendered to interfere with each other at the 3 dB coupler 325, and output as interference light from the first port 325a and the second port 325b. Here, the interference light output from the first port 325a and the interference light output from the second port 325b have a phase opposite from each other.

The interference light output from the first port 325a of the 3 dB coupler 325 passes through the second port 324b and the third port 324c of the optical circulator 324 and is input to the first port 337a of a Dual-balanced receiver 337 as the photoelectric conversion unit. Moreover, the interference light output from the second port 325b of the 3 dB coupler 325 is input to the second port 337b of the dual-balanced receiver 337. Thus, the dual-balanced receiver 337 photoelectrically converts interference light input respectively to the first port 337a and the second port 337b to obtain analog signals in which direct-current components have been cancelled and only interference components (alternating-current components) are existent. As the dual-balanced receiver 337, there is used one having an electric response band of 80 MHz, for example. It is noted that the polarization controller 327 provided in the reference-side optical transmission unit adjusts a polarization state of the reference light so that analog signals obtained from the dual-balanced receiver 337 are increased, that is, so that the reflected reference light and the reflected inspection light appropriately interfere with each other.

The analog signals output from the dual-balanced receiver 337 are input to a highpass filter (HPF) 338 as the analog signal process unit so that low-frequency components thereof are removed. The analog output signals from the HPF 338 are amplified by an amplifier 339 by about 10 dB, and then input to the A/D conversion unit 340 to be converted to digital signals. It is noted that there is used, as the A/D conversion unit 340, one with 14 bits and 100 MS/s, for example.

The digital output signals from the A/D conversion unit 340 are input to the image process unit 322. The image process unit 322 performs Fourier transformation for digital output signals from the A/D conversion unit 340 to calculate a power spectrum. The frequency is converted from a wavelength swept rate of the FDML 321 to the spatial distance in a depth direction of the object to be inspected 335, and the power is converted to the reflected and scattered light intensity in each depth position in the object to be inspected 335. As above, the image process unit 322 calculates and obtains the distribution between the spatial distance and the reflected and scattered light intensity in a depth direction, and generates a tomographic image of the object to be inspected 335 based on such data to display it on a monitor 341.

Thus, in the embodiment, the photoelectric conversion signals of interference light of the reflected reference light and the reflected inspection light obtained from the dual-balanced receiver 337 are input to the HPF 338 so that low-frequency components thereof are removed, and analog output signals from which the low-frequency components have been removed are amplified by the amplifier 339 and converted to digital signals by the A/D conversion unit 340, which makes it possible to convert information from the deep portion of the object to be inspected 335 to digital signals with emphasizing the information without burying it in quantization noise, thus improving the penetration depth of a tomographic image.

Eighteenth Embodiment

Figure 25:
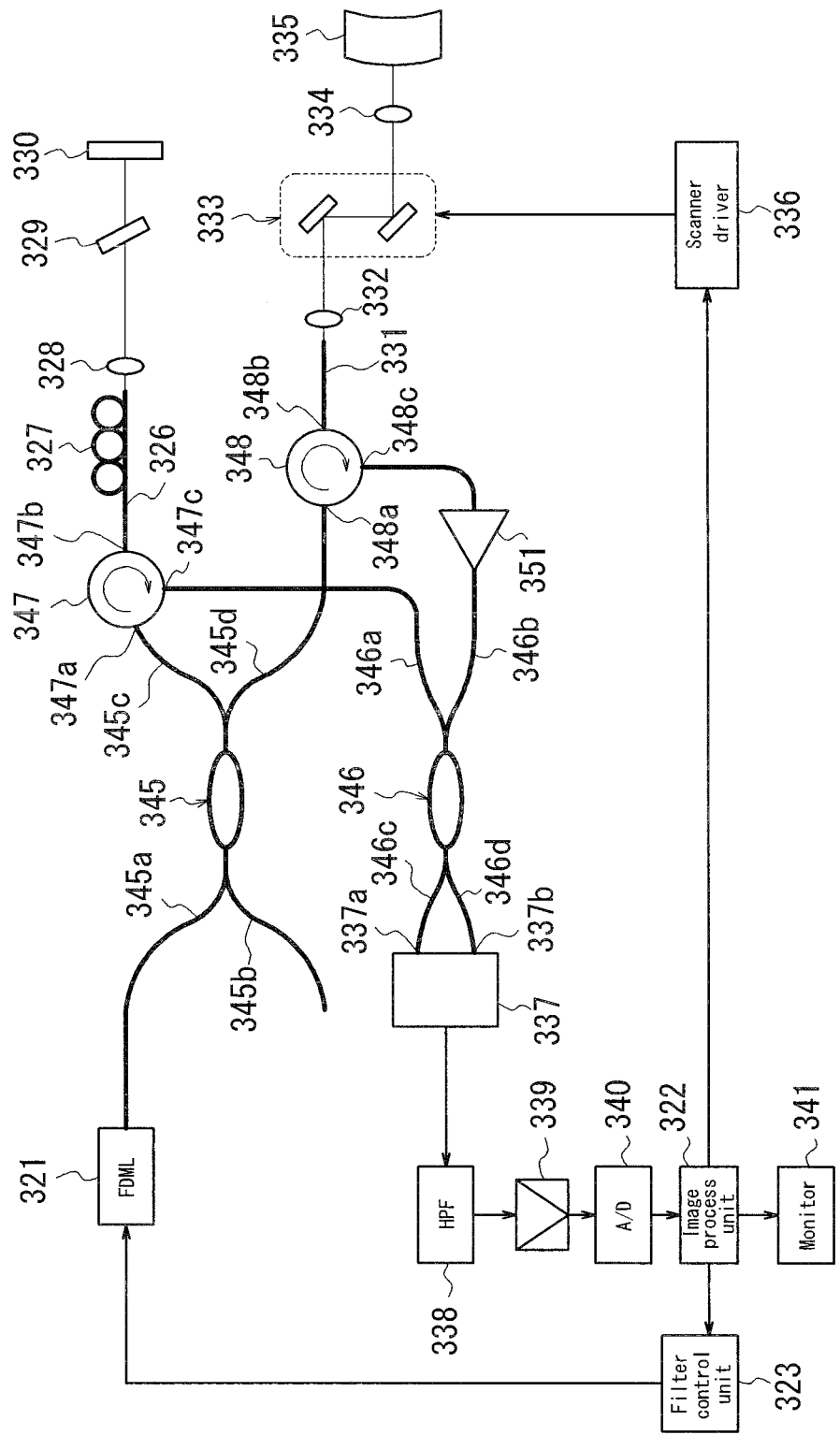
FIG. 25 is a functional block diagram illustrating a configuration of the optical tomographic image generation device according to the eighteenth embodiment of the invention.

FIG. 25 is a functional block diagram illustrating a configuration of the optical tomographic image generation device according to the eighteenth embodiment of the invention. With respect to the embodiment, in the first reference example, the reflected inspection light obtained from the object to be inspected 335 is amplified and then rendered to interfere with the reflected reference light. For this reason, with respect to the embodiment, optical multiplex-demultiplex unit is constituted by a 3 dB coupler 345 for optical demultiplex wave and a 3 dB coupler 346 for optical multiplex wave in the configuration shown in FIG. 24. In the following description, the components having a function same as of the component shown in FIG. 24 are represented with the same reference symbols, and the description thereof will be omitted.

In FIG. 25, the output end of the FDML 321 is connected to the first port 345a of the 3 dB coupler 345 for optical demultiplex wave, and the 3 dB coupler 345 demultiplexes light from the FDML 321 input to the first port 345a to the third port 345c and the fourth port 345d with an intensity ratio of 50:50 respectively.

The third port 345c of the 3 dB coupler 345 is connected to the first port 347a of an optical circulator 347, and reference light from the 3 dB coupler 345 is output from the second port 347b of the optical circulator 347. Moreover, the fourth port 345d of the 3 dB coupler 345 is connected to the first port 348a of the optical circulator 348, and inspection light from the 3 dB coupler 345 is output from the second port 348b of the optical circulator 348. It is noted that the second port 345b of the 3 dB coupler 345 is free.

The second port 347b of the reference-side optical circulator 347 is connected to the SMF 326, and the polarization state of reference light output from the second port 347b is adjusted by the polarization controller 327, in the same way as in the first reference example, thereafter the light passes through the lens 328 and the optical attenuator 329 and is reflected by the reflective mirror 330. The reflected reference light reflected by the reflective mirror 330 is rendered to be incident on the SMF 326 again through the optical attenuator 329 and the lens 328, input to the second port 347b of the optical circulator 347 and output from the third port 347c thereof.

On the other hand, the second port 348b of the inspection-side optical circulator 348 is connected to the SMF 331, and the inspection light output from the second port 348b through the SMF 331 passes through the lens 332, the galvano scanner mirror 333 and the lens 334 and is collected on the object to be inspected 335, in the same way as in the first reference example. With respect to the inspection light reflected and scattered by the object to be inspected 335 through irradiation for the object to be inspected 335 with inspection light, one part thereof passes through, as reflected inspection light, the lens 334, the galvano scanner mirror 333, the lens 332 and the SMF 331 again and is input to the second port 348b of the optical circulator 348 and output from the third port 348c thereof.

In the embodiment, the reflected inspection light from the object to be inspected 335 output from the third port 348c of the optical circulator 348 is amplified by an optical amplifier 351 by 10 dB, for example. As the optical amplifier 351, there is used a rare-earth-doped optical fiber amplifier using rare-earth-doped optical fibers, an optical fiber amplifier using Silica optical fibers such as the optical Raman amplifier or a semiconductor optical amplifier.

The third port 347c of the reference-side optical circulator 347 is connected to the first port 346a of the 3 dB coupler 346 for optical multiple wave. Moreover, the third port 348c of the inspection-side optical circulator 348 is connected to the second port 346b of the 3 dB coupler 346 for optical multiple wave. Thus, in the 3 dB coupler 346 for optical multiple wave, reflected reference light input to the first port 346a and the reflected inspection light input to the second port 346b are rendered to interfere with each other, and output from the third port 346c and the fourth port 346d.

The third port 346c and the fourth port 346d of the 3 dB coupler 346 are connected to the first port 337a and the second port 337b of the dual-balanced receiver 337 respectively to obtain analog signals in which direct-current components have been cancelled by the dual-balanced receiver 337 and only interference components (alternating-current components) are existent. The other configurations and operations are the same as in the first reference example.

According to the embodiment, the reflected inspection light obtained from the object to be inspected 335 is amplified by the optical amplifier 351 and then rendered to interfere with the reflected reference light, which makes it possible to extract information from the deep portion of the object to be inspected 335 and thus further improve the penetration depth of a tomographic image.

Nineteenth Embodiment

Figure 26:
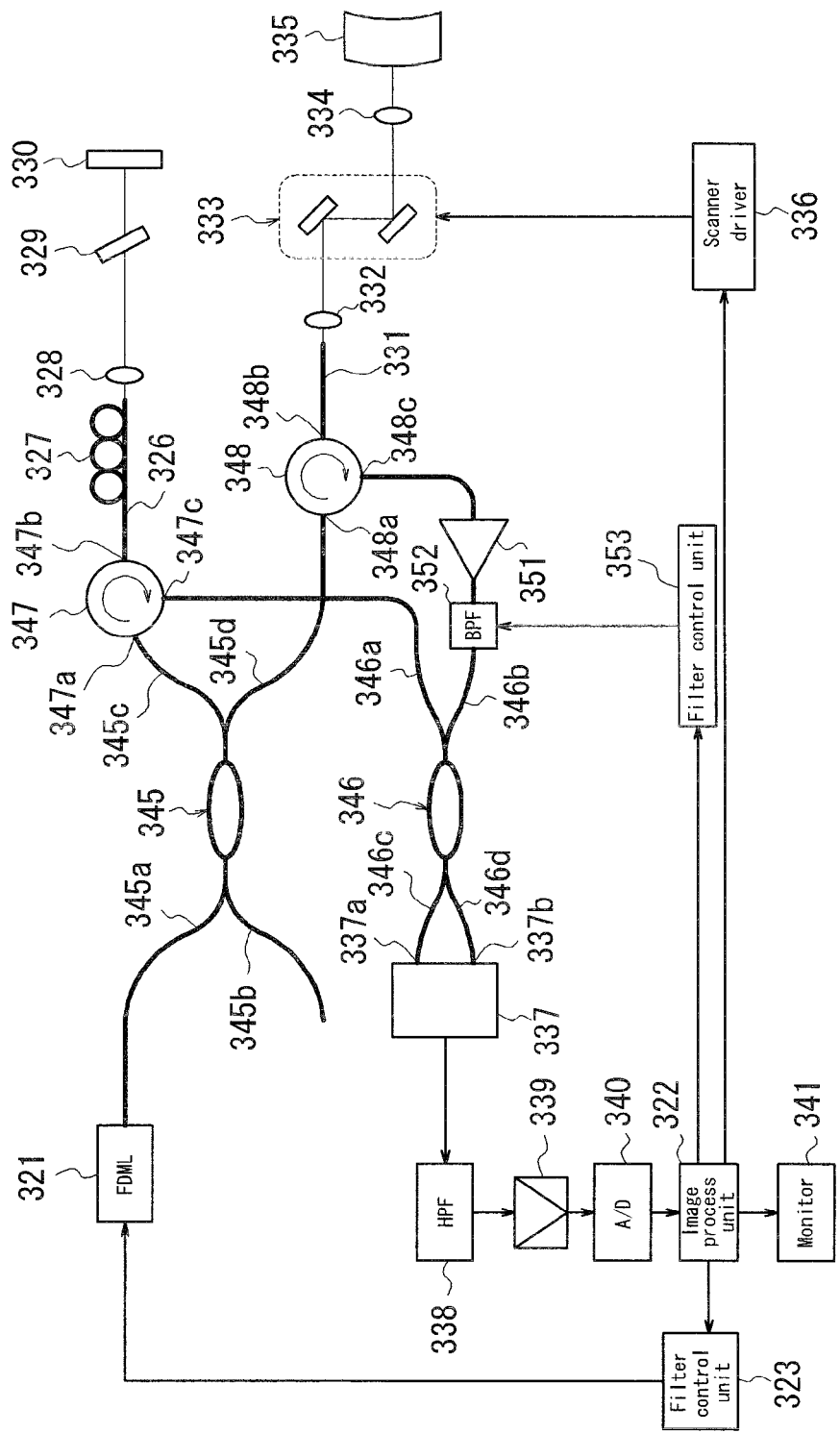
FIG. 26 is a functional block diagram illustrating a configuration of the optical tomographic image generation device according to the nineteenth embodiment of the invention.

FIG. 26 is a functional block diagram illustrating a configuration of the optical tomographic image generation device according to the nineteenth embodiment of the invention. With respect to the embodiment, an optical band-pass filter (BPF) 352 is disposed between the optical amplifier 351 and the second port 346b of the 3 dB coupler 346 for optical multiplex wave in the configuration of the eighteenth embodiment shown in FIG. 25. The optical BPF 352 has a dielectric multilayer having a transmitted wavelength bandwidth of 1 nm, for example, and is configured so that the transmitted central wavelength is variable by changing an angle of the dielectric multilayer relative to the incident light axis. With respect to the optical BPF 352, the image process unit 322 controls the angle of the dielectric multilayer relative to the incident light axis through the filter control unit 353, and varies the transmitted central wavelength in synchronization with variation with time of swept wavelength output from the FDML 321. That is, the transmitted central wavelength of the optical BPF 352 is controlled to have the same wavelength as one swept and output from the FDML 321. Since other configurations and operation are the same as in the eighteenth embodiment, the same components having a function same as of the components shown in FIG. 25 are represented with the same reference symbols, and the description thereof will be omitted.

Thus, in the embodiment, the reflected inspection light obtained from the object to be inspected 335 is amplified by the optical amplifier 351, thereafter the optical BPF 352 in which the transmitted wavelength is variable allows only reflected inspection light having a wavelength to be swept to pass therethrough, which enables lower noise of the reflected inspection light to be multiplexed with the reflected reference light. Therefore, information from the deep portion of the object to be inspected 335 can be extracted with higher accuracy.

It is noted that, for the inventions of the application disclosed in the eighteenth and nineteenth embodiments, many variations and modifications can be implemented. For example, the amplifier 339 can be disposed between the dual-balanced receiver 337 and the HPF 338. Moreover, the analog signal process unit is not limited to the HPF 338 and can be constituted using the BPF. Furthermore, in the first to third embodiments, there can be used, instead of the HPF 338 and the amplifier 339, the high-frequency amplifier having a low gain in a low-frequency band and a high gain in a high-frequency band.

Moreover, according to the thirty-ninth aspect of the application, as described in the above eighteenth and nineteenth embodiments, the photoelectric conversion signals of interference light of the reflected inspection light and the reflected reference light though SSOCT are provided to the analog signal process unit so that low-frequency components of the photoelectric conversion signals are attenuated relative to high-frequency components, and then the analog-digital conversion unit converts them to digital signals so that a tomographic image is generated, which makes it possible to convert information from the deep portion of the object to be inspected such as an organism or the like to digital signals with high accuracy without burying the information in quantization noises, thus improving the penetration depth of the tomographic image.

The invention claimed is:
1. An optical inspection device comprising:
 a light generation unit;
 a light irradiation unit irradiating an object to be inspected with light generated from the light generation unit;
 a photodetection unit photoelectrically converting signal light obtained from the object to be inspected through irradiation of light by the light irradiation unit, and inspecting the object to be inspected based on output from the photodetection unit;
 a light amplification unit amplifying signal light obtained from the object to be inspected;
 an optical multiplex-demultiplex unit demultiplexing light from the light generation unit to inspection light and reference light so that the object to be inspected is irradiated with the inspection light by the light irradiation unit and the reference light is guided to a light reflection unit, amplifying, by the light amplification unit, reflected inspection light obtained in a way that the inspection light is reflected and scattered by the object to be inspected, and multiplexing the amplified reflected inspection light and reflected reference light obtained in a way that the reference light is reflected by the light reflection unit so as to generate interference light;
 an analog signal process unit attenuating low-frequency components of photoelectric conversion signals obtained from the photodetection unit relative to high-frequency components thereof;
 an analog-digital conversion unit converting analog output signals from the analog signal process unit to digital signals; and
 an image process unit processing digital output signals from the analog-digital conversion unit so as to generate an optical tomographic image,
 wherein the light generation unit is a wavelength-variable light source unit emitting light whose wavelength varies with time; and
 the photodetection unit is a photoelectrical conversion unit receiving interference light generated by the optical multiplex-demultiplex unit and photoelectrically converting the same.

2. An optical inspection device according to claim 1, wherein the light amplification unit comprises a waveguide-type optical amplifier.

3. An optical inspection device according to claim 2, wherein the waveguide-type optical amplifier is constituted by a semiconductor optical amplifier.

4. An optical inspection device according to claim 2, wherein the waveguide-type optical amplifier is constituted by an optical fiber amplifier.

5. An optical inspection device according to claim 1, wherein the light amplification unit amplifies, as the signal light, light having a wavelength different from that of light with which the object to be inspected is irradiated.

6. An optical inspection device according to claim 5, wherein the light amplification unit amplifies, as the signal light, fluorescence or phosphorescence generated from the object to be inspected.

7. An optical inspection device according to claim 5, wherein the light amplification unit amplifies, as the signal light, light generated by nonlinear optical effects in the object to be inspected.

8. An optical inspection device according to claim 1, comprising a gain control unit controlling a gain of the light amplification unit in synchronization with timing of incidence of the signal light on the light amplification unit.

9. An optical inspection device according to claim 1, wherein the light amplification unit is configured so that a wavelength band of light to be amplified is narrower than that of light to be incident.

10. An optical inspection device according to claim 1, wherein a back reflection prevention unit preventing back reflection from the light amplification unit to the object to be inspected is provided at the input side of the light amplification unit.

11. An optical inspection device according to claim 1, wherein a wavelength selection unit selecting a wavelength of signal light to be photoelectrically converted by the photodetection unit is provided between the light amplification unit and the photodetection unit.

12. An optical inspection device according to claim 1, comprising an optical system connecting the object to be inspected with the light amplification unit in optical conjugation.

13. An optical inspection device according to claim 1, wherein the object to be inspected is an organism; and the light amplification unit amplifies, as the signal light, light modulated by the organism.

14. An optical inspection device according to claim 1, wherein the light generation unit generates laser light.

15. An optical inspection device according to claim 1, comprising an image display unit displaying an image based on output from the photodetection unit, wherein the light irradiation unit comprises a light scan unit scanning with light with which the object to be inspected is irradiated in at least two-dimensional direction; and an image of an area of the object to be inspected scanned by the light scan unit is displayed on the image display unit based on output from the photodetection unit.

16. An optical inspection device according to claim 1, wherein an optical filter removing optical noises is provided between the light amplification unit and the optical multiplex-demultiplex unit.

17. An optical inspection device according to claim 16, wherein the optical filter is constituted by a band-pass filter in which a transmitted central wavelength is variable; and the transmitted central wavelength is varied in synchronization with variation with time of wavelength of light emitted from the wavelength-variable light source unit.

18. An optical tomographic image generation device comprising the optical inspection device according to claim 1.

* * * * *